US009872897B2

(12) United States Patent
Nikolin et al.

(10) Patent No.: US 9,872,897 B2
(45) Date of Patent: Jan. 23, 2018

(54) SCHMALLENBERG VIRUS (SBV) VACCINE, METHODS OF PRODUCTION, AND USES THEREOF

(71) Applicant: Boehringer Ingelheim Vetmedica GmbH, Ingelheim am Rhein (DE)

(72) Inventors: Veljko Nikolin, Hannover (DE); Konrad Stadler, Celle (DE); Axel Lischewski, Ockenheim (DE); Alexander Brix, Hannover (DE); Jeffrey P. Knittel, Parkville, MO (US); Katharina Hedwig Toepfer, Hannover (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 15/158,790

(22) Filed: May 19, 2016

(65) Prior Publication Data

US 2016/0250317 A1 Sep. 1, 2016

Related U.S. Application Data

(62) Division of application No. 13/904,752, filed on May 29, 2013, now Pat. No. 9,370,562.

(30) Foreign Application Priority Data

Jun. 1, 2012 (EP) .................................... 12170631
Mar. 5, 2013 (EP) .................................... 13157875

(51) Int. Cl.

| | |
|---|---|
| ***A61K 39/12*** | (2006.01) |
| ***A61K 35/76*** | (2015.01) |
| ***A61K 47/22*** | (2006.01) |
| ***C07K 7/00*** | (2006.01) |
| *A61K 39/00* | (2006.01) |

(52) U.S. Cl.

CPC .............. *A61K 39/12* (2013.01); *A61K 35/76* (2013.01); *A61K 47/22* (2013.01); *C07K 7/00* (2013.01); *A61K 2039/5252* (2013.01); *A61K 2039/545* (2013.01); *A61K 2039/552* (2013.01); *A61K 2039/55505* (2013.01); *A61K 2039/55577* (2013.01); *C12N 2760/12021* (2013.01); *C12N 2760/12022* (2013.01); *C12N 2760/12034* (2013.01); *C12N 2760/12063* (2013.01)

(58) Field of Classification Search

None

See application file for complete search history.

(56) References Cited

U.S. PATENT DOCUMENTS

2008/0226682 A1 9/2008 Brake et al.
2013/0323210 A1 12/2013 Reimann et al.
2013/0323277 A1 12/2013 Nikolin et al.

FOREIGN PATENT DOCUMENTS

EP 0514199 A2 11/1992
JP S6341428 A 2/1988
WO 199707674 A1 3/1997
WO 2009065930 A1 5/2009
WO 2013181270 A1 12/2013

OTHER PUBLICATIONS

Kruger et al., Human pathogenic hantaviruses and prevention of infection, 2011, Human Vaccines, vol. 7, No. 6, pp. 685-693.*

Kim et al., Development of inactivated trivalent vaccine for the teratogenic Aino, Akabane and Chuzan viruses, 2011, Biologicals, vol. 39, pp. 152-157.*

Beer et al., "Update-Information from the Friedrich-Loeffler-Institut on 'Schmallenberg Virus': Accessions No. of full-length sequences available". Friedrich-Loeffler-Institut, Jan. 16, 2012, 1 page. [Accessed at http://www.fli.bund.de/fileadmin/dam_uploads/tierseuchen/Schmallenberg_Virus/Schmallenberg-Update_20120116-en.pdf on Jul. 9, 2013].

Bennett et al., "A Recombinant Chimeric La Crosse Virus Expressing the Surface Glycoproteins of Jamestown Canyon Virus Is Immunogenic and Protective against Challenge with either Parental Virus in Miche or Monkeys". Journal of Virology, vol. 86, No. 1, 2012, pp. 420-426.

Bridgen et al., "Rescue of a segmented negative-strand RNA virus entirely from cloned complementary DNAs". Procedures of the National Academy of Sciences, vol. 93, Dec. 1996, pp. 15400-15404.

Doceul et al., "Epidemiology, molecular virology and diagnostics of Schmallenberg virus, an emerging orthobunyavirus in Europe". Veterinary Research, vol. 44, No. 31, 2013, pp. 1-13.

Elliott et al., "Establishment of a reverse genetics system for Schmallenberg virus, a newly emerged orthobunyavirus in Europe". Journal of General Virology, vol. 94, No. 4, Apr. 2013, pp. 851-859.

EMBL Accession No. HE649912, Hoffman et al., "Schmallenberg virus RdRp gene for RNA-dependent RNA polymerase, segment L, genomic RNA, isolate BH80/11-4"., Frederick-Loeffler-Institute, Jan. 16, 2012, 4 pages.

EMBL Accession No. HE649913, Hoffman et al., "Schmallenberg virus gene for M polyprotein, segment M, genomic RNA, isolate BH80/11-4"., Frederick-Loeffler-Institute, Jan. 16, 2012, 3 pages.

EMBL Accession No. HE649914, Hoeper, D., "Schmallenberg virus genes for nucleocapsid protein and non-structural protein, segment S, genomic RNA, isolate BH80/11-4"., Frederick-Loeffler-Institute, Jan. 16, 2012, 2 pages.

Garigliany et al., "Schmallenberg virus: A new Shamonda/Sathuperi-like virus on the rise in Europe". Antiviral Research, vol. 95, No. 2, May 2012, pp. 82-87.

Hoffmann et al., "Novel Orthobunyavirus in Cattle, Europe, 2011". Emerging Infectious Diseases, vol. 18, No. 3, Mar. 2012, pp. 469-472.

Ikegami et al., "Rift Valley fever vaccines". Vaccine, vol. 27, Nov. 2009, pp. D69-D72.

(Continued)

*Primary Examiner* — Benjamin P Blumel

(74) *Attorney, Agent, or Firm* — Marc Began; Wendy M. Gombert

(57) ABSTRACT

The present invention relates to the field of vaccines and medicaments for the prophylaxis and treatment of infectious diseases in ruminants. In particular, it relates to inactivated Schmallenberg virus (SBV) useful as vaccine or medicament for preventing or treating viremia, the transmission and clinical symptoms, in particular malformations in newborn ruminants such as cattle, sheep and goats, induced by SBV.

8 Claims, No Drawings

(56) References Cited

OTHER PUBLICATIONS

International Search Report and Written Opinion for PCT/US2013/043146 dated Jul. 18, 2013.

Lytle et al., "Predicted Inactivation of Viruses of Relevance to Biodefense by Solar Radiation". Journal of Virology, vol. 79, No. 22, Nov. 2005, pp. 14244-14252.

Mettenleiter et al., "Information from the Friedrich-Loeffler-Institut on 'Schmallenberg Virus'". Friedrich-Loeffler-Institut, Jan. 10, 2012, 1 page. [Accessed at http://www.fli.bund.de/fileadmin/dam_uploads/tierseuchen/Schmallenberg_Virus/FLIInformation_Schmallenberg-20120110.pdf on Jul. 9, 2013].

Varela et al., "Schmallenberg Virus Pathogenesis, Tropism and Interaction with the Innate Immune System of the Host". PLOS Pathogens, vol. 9, No. 1, e1003133, Jan. 2013, pp. 1-13.

Wernike et al., "Inactivated Schmallenberg virus prototype vaccines". Vaccine, vol. 31, May 2013, pp. 3558-3563.

Wernike et al., "Schmallenberg virus challenge modesI in cattle: infectious serum or culture-grown virus". Veterinary Research, vol. 43, No. 1, Dec. 2012, pp. 84-87.

Yanase et al., "Genetic reassortment between Sathuperi and Shamonda viruses of the genus Orthobunyavirus in nature: implications for their genetic relationship to Schmallenberg virus". Archives of Virology, vol. 157, No. 8, May 2012, pp. 1611-1616.

Abstract in English of JPS6341428A, 1988.

Hsieh et al., "DNA Sequence Analysis of Glycoprotein G Gene of Bovine Ephemeral Fever Virus and Development of a Double Oil Emulsion Vaccine against Bovine Ephemeral Fever". The Journal of Veterinary Medical Science, vol. 68, No. 6, 2006, pp. 543-548.

Wikipedia contributors. "Bunyaviridae". Wikipedia, The Free Encyclopedia, Jun. 23, 2017, 15:48 UT, pp. 1-6 Accessed at https://en.wikipedia.org/w/index.php?title=Bunyaviridae&oldid=787124665 on Aug. 28, 2017.

Coupeau et al., "In vivo and in vitro identification of a hypervariable region in Schmallenberg virus." Journal of General Virology, vol. 94, 2013, pp. 1168-1174.

Fischer et al., "A mutation 'hot spot' in the Schmallenberg virus M segment" Journal of General Virology, vol. 94, 2013, pp. 1161-1167.

Wu et al., "A Review of Research on Schmallenberg Virus." Chinese Journal of Virology, vol. 30, No. 6, pp. 694-703. Abstract in English on p. 703), 2014.

* cited by examiner

SCHMALLENBERG VIRUS (SBV) VACCINE, METHODS OF PRODUCTION, AND USES THEREOF

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Technical Field

The present invention belongs to the field of vaccines and medicaments for the prophylaxis and treatment of infectious diseases. In particular, it relates to inactivated viruses useful as vaccine or medicament for preventing or treating viremia, the transmission and clinical symptoms, in particular malformations in newborn ruminants such as cattle, sheep and goats, induced by Schmallenberg virus.

Background Information

A novel orthobunyavirus, the Schmallenberg virus (SBV), was discovered in Europe in November 2011. After the first detection, the reported cases of SBV in sheep, cattle, and goats dramatically accumulated in several European countries to several thousand cases of PCR-positive malformed lambs and calves (1, 2). The virus was detected by metagenomics at the Friedrich-Loeffler-Institut (FLI) in samples of cattle with milk drop and fever. The investigated samples were collected in a farm near the city of Schmallenberg (North Rhine-Westphalia, Germany), and consequently the virus was named Schmallenberg virus (SBV). SBV is a member of the genus Orthobunyavirus within the family Bunyaviridae. It is related to the so-called Simbu serogroup viruses (1).

Orthobunyaviruses have a segmented, negative stranded RNA genome and are mainly transmitted by insect vectors like midges and mosquitos. The three segments (S, M and L) of the Orthobunyavirus genome allow genetic reassortment, which naturally occurs resulting in the emergence of viruses with new biological properties (3). The largest segment L encodes the RNA-dependent RNA polymerase. The M-segments encodes the viral surface glycoproteins Gn and Gc which are responsible for cell fusion, viral attachment and the induction of neutralizing antibodies. The small S-segment encodes the nucleocapsid N which is also involved in complement fixation (4). The relationship between Orthobunyaviruses was often only determined by serological cross-reactivity (5). In the era of DNA sequencing, phylogenetics has additionally been assessed by comparison of partial genome sequences (full N and partial Gc gene) (6). Therefore, available and published genome sequence information of full-length genomes is sparse. As a consequence, in-depth phylogenetic analyses are difficult. In conclusion, a detailed and reliable taxonomic classification of SBV could not be made. Preliminary investigations showed similarities of the M- and L-segment sequences to partial AKAV and Aino virus (AINOV) sequences. The N gene was most closely related to Shamonda virus (SHAV) (1).

SBV is like Akabane virus (AKAV) able to cross the placental barrier in pregnant cows and sheep, infect the fetus and cause fatal congenital defects during a susceptible stage in pregnancy (2). The Simbu serogroup, named after the prototype virus, is the largest serogroup of Orthobunyavirus and contains at least 25 viruses, among them medically important viruses such as Akabane virus, Oropouche virus, Sathuperi virus or Douglas virus, most of which can cause malformations in new born ruminants, but also human beings can be affected. Akabane virus, for instance, causes congenital defects in ruminants and circulates in Asia, Oceania and Africa, whereas Oropouche virus is responsible for large epidemics of Oropouche fever, a zoonosis similar to dengue fever, in human populations in South America. Sathuperi virus has lent his name to the Sathuperi serogroup, to which belong also Douglas virus and SBV.

SBV was the first orthobunyavirus of the Simbu serogroup detected in Europe. The virus is apparently transmitted by arthropod vectors. Biting midges probably play an important role in transmission. According to the current state of knowledge, ruminants are susceptible to infection with SBV. Adult animals may develop mild disease, if any. However, transplacental infection occurs frequently and can lead to severe congenital malformation of the vertebral column (Kyphosis, lordosis, scoliosis, torticollis) and of the scull (macrocephaly, brachygnathia inferior) as well as variable malformations of the brain (hydracephaly, porencephaly, cerebellar hypoplasia, hypoplasia of the brain stem) and of the spinal cord in lambs, kids and calves. The infection spread rapidly over large parts of North Western Europe. Belgium, Germany, France, Italy, Luxembourg, the Netherlands, Spain and the United Kingdom have been affected so far.

Therefore, SBV is a serious threat to ruminant livestock in Europe since vaccines are currently not available.

Thus, there is a strong need for vaccines and medications effecting a rapid induction of neutralizing antibodies for the prophylaxis and treatment of Schmallenberg virus infection.

DESCRIPTION OF THE INVENTION

The solution to the above technical problem is achieved by the description and the embodiments characterized in the claims.

Thus, the invention in its different aspects is implemented according to the claims.

In one aspect, the invention provides an immunogenic composition containing one or more antigens of the Schmallenberg virus (SBV), wherein the immunogenic composition preferably comprises the SBV.

Preferably, SBV is thus contained as the one or more antigens of SBV in the composition of the invention, or the one or more antigens of the SBV is/are preferably SBV, respectively. Hence, the immunogenic composition of the invention is in particular an immunogenic composition comprising Schmallenberg virus (SBV).

As used herein, the term "antigen" in particular refers to any molecule, moiety or entity capable of eliciting an immune response. This includes cellular and/or humoral immune responses. Depending on the intended function of the composition, one or more antigens may be included be included.

In a further preferred aspect, the antigen of SBV or the SBV contained in the immunogenic composition of the invention is inactivated.

According to one aspect, the immunogenic composition of the invention is thus preferably an immunogenic composition comprising inactivated Schmallenberg virus (SBV).

The term "inactivated", as used herein, means that the antigen does not cause disease, when administered to a mammalian host or does not replicate in a host cell.

The invention also provides an immunogenic composition comprising SBV or an antigen of SBV, wherein the SBV comprises

- a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7,
- a medium (M) RNA segment having a sequence that is inverse complementary to a nucleic acid sequence having at least 82.2% sequence identity with the nucleic acid sequence of SEQ ID NO:2, and/or
- a large (L) RNA segment having a sequence that is inverse complementary to a nucleic acid sequence having at least 93% sequence identity with the nucleic acid sequence of SEQ ID NO:3.

Preferably, said SBV comprises said small (S) RNA segment, said medium (M) RNA segment and said (L) RNA segment.

According to another aspect, the SBV or the antigen of the SBV is obtainable by the inactivation of SBV or the antigen of SBV, wherein said SBV comprises

- a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7,
- a medium (M) RNA segment having a sequence that is inverse complementary to a nucleic acid sequence having at least 82.2% sequence identity with the nucleic acid sequence of SEQ ID NO:2, and/or
- a large (L) RNA segment having a sequence that is inverse complementary to a nucleic acid sequence having at least 93% sequence identity with the nucleic acid sequence of SEQ ID NO:3.

All sequences of the sequence listing are typed in 5'-'3 direction. The sequences of SEQ ID NOs. 1 to 3 and 7 code for cDNAs having a positive polarity (+strand). The term "inverse complementary" means that the sequence is anti-parallel to the reference sequence.

Preferably said SBV comprises said small (S) RNA segment, said medium (M) RNA segment and said (L) RNA segment.

It is understood that the term "RNA segment", as used herein, is equivalent to "genome segment" or "segment", as frequently used in the context of Schmallenberg virus.

Preferably, the small (S) RNA segment mentioned herein has an RNA sequence that is inverse complementary to a DNA sequence having at least 97.8%, more preferably at least 98.5%, even more preferably at least 99%, still more preferably at least 99.5% or in particular 100% sequence identity with the nucleic acid sequence of SEQ ID NO:1, or preferably, the small (S) RNA segment described herein has an RNA sequence that is inverse complementary to a DNA sequence having at least 97.8%, more preferably at least 98.5%, even more preferably at least 99%, still more preferably at least 99.5% or in particular 100% sequence identity with the nucleic acid sequence of SEQ ID NO:7.

Preferably, the medium (M) RNA segment mentioned herein has an RNA sequence that is inverse complementary to a DNA sequence having at least 83%, more preferably at least 85%, even more preferably at least 90%, still more preferably at least 95% or in particular 100% sequence identity with the nucleic acid sequence of SEQ ID NO:2.

Preferably, the large (L) RNA segment mentioned herein has an RNA sequence that is inverse complementary to a DNA sequence having at least 94%, more preferably at least 96%, still more preferably at least 98% or in particular 100% sequence identity with the nucleic acid sequence of SEQ ID NO:3.

As used herein, the term "immunogenic composition" in particular refers to a composition that will elicit an immune response in a mammal and/or an insect that has been exposed to the composition. An immune response may include induction of antibodies and/or induction of a T-cell response.

Sequence identity in the context of the invention is understood as being based on pairwise sequence alignments. For purposes of the present invention, pairwise sequence alignments are done with ClustalW as implemented in Mega5 (K. Tamura et. al., MEGA5: Molecular Evolutionary Genetics Analysis using Maximum Likelihood, Evolutionary Distance, and Maximum Parsimony Methods. Mol. Biol. Evol. 28, 2731-2739 (2011)), using the default settings (gap opening penalty of 15 and gap extension penalty of 6.66; DNA weight matrix: ClustalW 1.6; Transition weight of 0.5). Sequence identities of the aligned sequences are calculated using BioEdit version 7.0.9.0.

It is understood that the term "sequence identity to", as used herein, herein, is equivalent to the term "sequence identity with the nucleic acid sequence of". Thus, as mentioned herein, the term "sequence identity to SEQ ID NO:4 or SEQ ID NO:8" is equivalent to the term "sequence identity with the nucleic acid sequence of SEQ ID NO:4 or SEQ ID NO:8", the term "sequence identity to SEQ ID NO:5" is equivalent to the term "sequence identity with the nucleic acid sequence of SEQ ID NO:5", and the term "sequence identity to SEQ ID NO:6" is equivalent to the term "sequence identity with the nucleic acid sequence of SEQ ID NO:6".

As used herein, it is in particular understood that the term "sequence identity with the nucleic acid sequence of SEQ ID NO:X" is equivalent to the term "sequence identity with the nucleic acid sequence of SEQ ID NO:X over the length of SEQ ID NO: X" or to the term "sequence identity with the nucleic acid sequence of SEQ ID NO:X over the whole length of SEQ ID NO: X", respectively. In this context, "X" is any integer selected from 1 to 8 so that "SEQ ID NO: X" represents any of the SEQ ID NOs mentioned herein.

In a further preferred aspect of the invention, the SBV mentioned herein comprises

- an S RNA segment, characterized in that the S RNA segment has a sequence having at least 97.8%, preferably at least 99% sequence identity to SEQ ID NO:4 or SEQ ID NO:8,
- an M RNA segment, characterized in that the M RNA segment has a sequence having at least 82.2% sequence identity to SEQ ID NO:5, and/or
- an L RNA segment, characterized in that the L RNA segment has a sequence having at least 93% sequence identity to SEQ ID NO:6, and wherein in particular said SBV comprises said small (S) RNA segment, said medium (M) RNA segment and said (L) RNA segment.

Preferably, the SBV mentioned herein comprises

- an S RNA segment, characterized in that the S RNA segment has
- an RNA sequence having at least 97.8%, more preferably at least 98.5%, even more preferably at least 99%, still more preferably at least 99.5% or in particular 100% sequence identity to SEQ ID NO:4, or
- an RNA sequence having at least 97.8%, more preferably at least 98.5%, even more preferably at least 99%, still more preferably at least 99.5% or in particular 100% sequence identity to SEQ ID NO:8; and/or
- an M RNA segment, characterized in that the M RNA segment has a RNA sequence having at least 83%, more preferably at least 85%, even more preferably at least 90%, still more preferably at least 95% or in particular 100% sequence identity to SEQ ID NO:5; and/or an L RNA segment, characterized in that the L RNA segment has a RNA sequence having at least 94%, more preferably at least 96%, still more preferably at least 98% or in particular 100% sequence identity to SEQ ID NO:6.

The term "having 100% sequence identity", as used herein, is also understood to be equivalent to the term "being identical".

Preferably, the inactivated SBV is obtainable by the inactivation of SBV by heat treatment or preferably with a virus inactivating agent, wherein in particular an aziridine compound, most preferably binary ethyleneimine (BEI), is used for the inactivation.

According to one preferred aspect, BEI is added to the antigen in a final concentration of 10 mM or less, wherein it has been surprisingly found that a final concentration of less than 4 mM is sufficient for the inactivation of the antigen. Thus, BEI is preferably added to a final concentration of less than 4 mM to the antigen, more preferably to a final concentration of 0.5 to 3.5 mM, most preferably to a final concentration of 1 to 3 mM.

After the addition of BEI, the mixture is preferably kept in agitation for 48 h or less, preferably for 24 h or less, most preferably for between 6 h and 18 h, such as e.g. for 12 h. The temperature of the mixture while the mixture is being agitated is preferably 37+/−5° C., most preferably 37+/−1° C.

Further, it has been found that only one inactivation step, e.g. by adding BEI to the antigen, is sufficient for the inactivation of the antigen.

After the inactivation procedure, the residual virus inactivating agent is preferably neutralized by adding a neutralizing agent to the mixture, in particular in a molar excess in comparison to the amount of virus inactivating agent added to the antigen. If an aziridine compound is used for the inactivation, then preferably a nucleophile which opens the three-membered ring is used for the neutralization. BEI is preferably neutralized by the addition of sodium thiosulphate, in particular in a 1.1 to 10 fold molar excess, most preferably in a 2 to 8 fold molar excess in comparison to the amount of BEI added to the antigen.

In a preferred aspect, the immunogenic composition of the invention comprises an amount of SBV which is equivalent to a virus titre of at least about $10^{5.5}$ $TCID_{50}$/mL per dose, preferably between $10^5$ to $10^7$ $TCID_{50}$/mL per dose, more preferably about $10^6$ $TCID_{50}$/mL per dose.

Surprisingly, it has been found that an immunogenic composition of the invention comprising an amount of SBV which is equivalent to a virus titre of less than $10^{S5}$ $TCID_{50}$/ml per dose, preferably less than $10^5$ $TCID_{50}$/ml per dose, is sufficient to prevent SBV RNAemia in an animal, in particular in sheep.

Thus, the immunogenic composition of the invention preferably comprises an amount of SBV which is equivalent to a virus titre of less than $10^{5.5}$ $TCID_{50}$/ml per dose, preferably less than $10^5$ $TCID_{50}$/ml per dose, more preferably between $10^3$ to $10^5$ $TCID_{50}$/mL per dose, most preferably between $10^4$ to $10^5$ $TCID_{50}$/mL per dose, in particular for use in a method for inducing an immune response against SBV and/or for preventing or reducing viremia or malformations induced by SBV and/or for preventing or reducing the transmission of SBV, preferably in sheep.

"RNAemia" as described herein is in particular understood as the detection of RNA (e.g., by nucleic acid sequence-based amplification or reverse transcription PCR) in a sample of an animal, in particular in samples of plasma, serum or whole blood.

It is thus in particular understood, according to the invention, that viremia induced by SBV goes hand in hand or is accompanied, respectively, with SBV RNAemia in a sample of blood serum of an animal. Hence, viremia induced by SBV can be examined by detecting specific SBV RNA in the serum of animals.

In another preferred aspect, the immunogenic composition of the invention contains SBV having a pre-inactivation titre of at least about $10^6$ SBV particles per milliliter, preferably between $10^6$ to $10^8$ $TCID_{50}$/mL SBV particles per milliliter, more preferably about $10^7$ SBV particles per milliliter.

The term "pre-inactivation titre", as used herein, in particular refers to the amount of suspended SBV which is inactivated.

In particular, the immunogenic composition of the invention, further contains one or more pharmaceutically acceptable carriers or excipients, wherein said one or more pharmaceutically acceptable carriers or excipients are preferably selected from the group consisting of solvents, dispersion media, adjuvants, stabilizing agents, diluents, preservatives, antibacterial and antifungal agents, isotonic agents, and adsorption delaying agents.

In a particular preferred aspect, the immunogenic composition of the invention further contains one or more adjuvants, preferably aluminium hydroxide and/or saponin, e.g. Alhydrogel and/or Quil-A, wherein a combination of aluminium hydroxide and saponin is most preferred.

Another aspect concerns the immunogenic composition of the invention for use as a medicament, preferably as a vaccine.

A further aspect relates to the immunogenic composition of the invention for use in a method for inducing an immune response against SBV and/or for preventing or reducing viremia or malformations induced by SBV and/or for preventing or reducing the transmission of SBV.

This aspect in particular relates to the immunogenic composition of the invention for use in a method for inducing an immune response against SBV in a ruminant and/or insect and/or for preventing or reducing viremia in a ruminant and/or insect and/or for preventing or reducing malformations induced by SBV in a ruminant fetus or newborn and/or for preventing or reducing the transmission of SBV by arthropod vectors, preferably insects and/or for preventing or reducing the transmission of SBV from the pregnant animal (the mother) to the fetus.

As used herein, the term "inducing an immune response" to an antigen or composition is the development of a humoral and/or cellular immune response in an animal to an antigen present in the composition of interest.

The term "prevention" or "reduction" or "preventing" or "reducing", respectively, as used herein, means, but is not limited to a process which includes the administration of a SBV antigen, namely of the antigen of SBV according to the invention which is included in the composition of the invention, to an animal, wherein said SBV antigen, when administered to said animal elicits or is able to elicit an immune response in said animal against SBV. Altogether, such treatment results in reduction of the clinical signs of a disease caused by SBV or of clinical signs associated with SBV infection, respectively. More specifically, the term "prevention" or "preventing", as used herein, means generally a process of prophylaxis in which an animal is exposed to the immunogenic composition of the present invention prior to the induction or onset of the disease process caused by SBV.

Herein, "reduction of clinical signs associated with SBV infection" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of pathogen load, pathogen shedding, reduction in pathogen transmission, or reduction of any clinical sign symptomatic of SBV infection, in particular of the transmission of SBV from the mother to the fetus or of the malformations induced by SBV in a ruminant fetus or newborn. Preferably these clinical signs are reduced in subjects receiving the composition of the present invention by at least 10% in comparison to subjects not receiving the composition and may become infected. More preferably, clinical signs are reduced in subjects receiving the composition of the present invention by at least 20%, preferably by at least 30%, more preferably by at least 40%, and even more preferably by at least 50%.

The term "reduction of viremia induced by SBV" (or, alternatively, "reduction of RNAemia induced by SBV") means, but is not limited to, the reduction of SBV virus entering the bloodstream of an animal, wherein the viremia level, i.e. the number of SBV RNA copies per mL of blood serum or the number of plaque forming colonies per deciliter of blood serum, is reduced in the blood serum of subjects receiving the composition of the present invention by at least 50% in comparison to subjects not receiving the composition and may become infected. More preferably, the viremia level is reduced in subjects receiving the composition of the present invention by at least 90%, preferably by at least 99.9%, more preferably by at least 99.99%, and even more preferably by at least 99.999%.

As used herein, the term "viremia" is particularly understood as a condition in which Schmallenberg virus particles reproduce and circulate in the bloodstream of an animal, in particular of a mammal or of an insect.

The term "animal", as used herein, in particular relates to a mammal or to an insect.

Preferably, the mammal as mentioned herein is a ruminant. More preferably, the ruminant as mentioned herein is selected from the group consisting of cattle, sheep, goats, deer, elk, giraffes, bison, moose, yaks, water buffalo, camels, alpacas, llamas, antelope, pronghorn, and nilgai. Most preferably, the mammal or ruminant as mentioned herein is selected from the group consisting of cattle, sheep and goats.

The insect, as mentioned herein, is preferably selected from the group consisting of midges, in particular *Culicoides* spp., biting flies and mosquitoes.

Further, the invention provides a vaccine composition for the treatment or prevention of SBV or for the prevention or reduction of the viremia of malformations induced by SBV and/or for the prevention or reduction of the transmission of SBV, wherein the vaccine comprises the immunogenic composition of the invention.

In particular, the invention provides a vaccine composition, which comprises the immunogenic composition of the invention, for use in a method for inducing an immune response against SBV in a ruminant and/or insect and/or for preventing or reducing viremia in a ruminant and/or insect and/or for preventing or reducing malformations induced by SBV in a ruminant fetus or newborn and/or for preventing or reducing the transmission of SBV by arthropod vectors, preferably insects.

The term "malformations", as used herein, in particular relates to a malformation selected from congenital malformation of the vertebral column (Kyphosis, lordosis, scoliosis, torticollis) and/or of the scull (macrocephaly, brachygnathia inferior), variable malformations of the brain (hydracephaly, porencephaly, cerebellar hypoplasia, hypoplasia of the brain stem) and of the spinal cord, malformations and/or stiffening of fore and/or hind legs. More particular, the term "malformations" relates to malformations in lambs, kids and calves.

The invention also provides a method for the production of infectious SBV, comprising the steps of infecting cells, preferably mammalian or insect cells, with a SBV, cultivating the infected cells, harvesting the SBV produced by said cells.

The term "infecting", as used herein, in particular refers to the process of contacting cells with SBV, such as by inoculation.

Said infection of the cells with a SBV in particular includes attachment of the virus to a cell, entry of the virus into the cell, uncoating of the virion in the cytoplasm, replication and transcription of the viral genome, expression of viral proteins and assembly and release of new infectious viral particles.

The term "cultivating", as used herein, is particularly directed to the maintenance and preferably the growth of cells under suitable conditions.

The term "harvesting", as used herein, in particular refers to the taking of cell supernatant which contains viral particles, such as by centrifugation of a container containing a culture of virus infected cells and subsequent decantation of the cell supernatant.

Surprisingly, it has been found that SBV remains infectious, and thus also remains its antigenic potential, when it is alternately passaged between insect cells and mammalian cells.

Thus, the invention in particular concerns a method for the production of preferably infectious SBV, in particular the above-mentioned method, wherein the SBV is passaged alternately between insect cells and mammalian cells.

Hence, the method for the production of infectious SBV according to the invention in particular comprises the steps of:

(a) infecting insect cells with a SBV, (b) cultivating the infected cells of step (a), (c) harvesting the SBV produced by said cells in step (b), (d) infecting mammalian cells with the SBV harvested in step (c), (e) cultivating the infected cells of step (d), and (f) harvesting the SBV produced by said cells in step (e)

or comprises the steps of (d) infecting mammalian cells with a SBV, (e) cultivating the infected cells of step (d), (f) harvesting the SBV produced by said cells in step (e)

(g) infecting insect cells with the SBV harvested in step (f), (h) cultivating the infected cells of step (g), and (i) harvesting the SBV produced by said cells in step (h).

In this regard, the numeration of the steps (d)-(i) is equivalent to the numeration (a')-(f') and has been chosen for reasons of clarity in view of the further steps described herein (starting with the step "(j)").

Preferably, the method for the production of SBV of the invention comprises the steps of:

(a) infecting insect cells with a SBV,
(b) cultivating the infected cells of step (a),
(c) harvesting the SBV produced by said cells in step (b)
(d) infecting mammalian cells with the SBV harvested in step (c),
(e) cultivating the infected cells of step (d),
(f) harvesting the SBV produced by said cells in step (e)
(g) infecting insect cells with the SBV harvested in step (f)
(h) cultivating the infected cells of step (g), and
(i) harvesting the SBV produced by said cells in step (h).

More preferably, the method for the production of infectious SBV according to the invention further comprises the steps of (j) infecting mammalian cells with the SBV harvested in step (i),
(k) cultivating the infected cells of step (j), and
(l) harvesting the SBV produced by said cells in step (k), and optionally
(m) infecting insect cells with the SBV harvested in step (l),
(n) cultivating the infected cells of step (m), and
(o) harvesting the SBV produced by said cells in step (n).

Thus, in one aspect, the method for the production of infectious SBV according to the invention comprises the steps of (a) infecting insect cells with a SBV,
(b) cultivating the infected cells of step (a),
(c) harvesting the SBV produced by said cells in step (b)
(d) infecting mammalian cells with the SBV harvested in step (c),
(e) cultivating the infected cells of step (d),
(f) harvesting the SBV produced by said cells in step (e)
(g) infecting insect cells with the SBV harvested in step (f)
(h) cultivating the infected cells of step (g),
(i) harvesting the SBV produced by said cells in step (h)
(j) infecting mammalian cells with the SBV harvested in step (i),
(k) cultivating the infected cells of step (j), and
(l) harvesting the SBV produced by said cells in step (k), and optionally
(m) infecting insect cells with the SBV harvested in step (l),
(n) cultivating the infected cells of step (m), and
(o) harvesting the SBV produced by said cells in step (n).

The insect cells used in the method for the production of SBV of the invention are preferably KC cells.

As mammalian cells preferably BHK cells, in particular BHK-21 cells, are used in the method for the production of SBV according to the invention.

Most preferably, in the method for the production of SBV according to the invention the insect cells are KC cells, and the mammalian cells are BHK cells, in particular BHK-21 cells.

Further, the invention also comprises the SBV obtainable by the method for the production of SBV according to the invention.

The invention further provides a method for the production of inactivated SBV or of an immunogenic composition of the invention comprising the steps of:

(A) infecting cells with a SBV, wherein the cells are in particular monkey kidney cells, preferably Ma104 cells or Ma104-AK cells, or wherein the cells are BHK cells, preferably BHK-21 cells,
(B) cultivating the infected cells,
(C) harvesting the SBV produced by said cells, and
(D) inactivating said SBV by heat treatment or with a virus inactivating agent If preferably Ma104 cells or Ma104-AK cells are used in the method for the production of inactivated SBV or of the immunogenic composition of the invention, this has the advantage that adverse reactions, in particular allergic reactions, can be reduced or minimized if the inactivated SBV or the immunogenic composition produced by said method is administered to an animal.

In particular, it is preferred if in step (A) of the method for the production of inactivated SBV or of the immunogenic composition of the invention the cells are infected with a SBV obtainable by the method for the production of SBV of the invention.

The invention thus also provides the combination of (i) the method of producing an infectious SBV of the invention and (ii) the method for the production of inactivated SBV or of the immunogenic composition of the invention, wherein said methods are performed subsequently.

Preferably, in the method for the production of infectious SBV of the invention and/or in the method for the production of inactivated SBV or of the immunogenic composition according to the invention, the cells are infected with SBV at an MOI of 0.00001-0.01, preferably at an MOI of 0.0001-0.001.

In particular it is preferred, if in the method for the production of SBV according to the invention and/or in the method for the production of inactivated SBV or of the immunogenic composition of the invention, the cells are cultivated in a medium containing 1-10% FCS, more preferably containing 2-6% FCS, and/or if the cells are cultivated at a temperature of 25-38° C., preferably of 36-38° C., more preferably of about 37° C. It is also possible to cultivate the cells in the absence of FCS.

Also, the invention comprises SBV obtainable by the method for the production of inactivated SBV or of the immunogenic composition of to the invention, and, moreover, the invention also provides inactivated SBV obtainable by the combination of (i) the method of producing an infectious SBV of the invention and (ii) the method for the production of inactivated SBV or of the immunogenic composition of the invention, where said methods are performed subsequently.

In another aspect, it is preferred if in the method for the production of infectious SBV of the invention and/or in the method for the production of inactivated SBV or of the immunogenic composition of the invention, the SBV comprises a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7, a medium (M) RNA segment having a sequence that is inverse complementary to a nucleic acid sequence having at least 82.2% sequence identity with the nucleic acid sequence of SEQ ID NO:2, and/or a large (L) RNA segment having a sequence that is inverse complementary to a nucleic acid sequence having at least 93% sequence identity with the nucleic acid sequence of SEQ ID NO:3, and/or wherein said SBV comprises an S RNA segment, characterized in that the S RNA segment has a sequence having at least 97.8%%, preferably at least 99% sequence identity to SEQ ID NO:4 or SEQ ID NO:8, an M RNA segment, characterized in that the M RNA segment has a sequence having at least 82.2% sequence identity to SEQ ID NO:5, and/or an L RNA segment, characterized in that the L RNA segment has a sequence having at least 93% sequence identity to SEQ ID NO:6.

The invention also provides a SBV, preferably an isolated SBV, comprising a small (S) RNA segment having a sequence that is inverse complementary to a nucleic acid sequence having at least 97.8%, preferably at least 99% sequence identity with the nucleic acid sequence of SEQ ID NO:1 or SEQ ID NO:7, a medium (M) RNA segment having a sequence that is inverse complementary to a nucleic acid sequence having at least 82.2% sequence identity with the nucleic acid sequence of SEQ ID NO:2, and/or a large (L) RNA segment having a sequence that is inverse complementary to a nucleic acid sequence having at least 93% sequence identity with the nucleic acid sequence of SEQ ID NO:3.

The invention further provides a preferably isolated SBV, in particular the aforementioned SBV, which comprises an S RNA segment, characterized in that the S RNA segment has a sequence having at least 97.8% sequence identity to SEQ ID NO:4 or SEQ ID NO:8, an M RNA segment, characterized in that the M RNA segment has a sequence having at least 82.2% sequence identity to SEQ ID NO:5, and/or an L RNA segment, characterized in that the L RNA segment has a sequence having at least 93% sequence identity to SEQ ID NO:6.

Also the invention comprises a composition of matter obtainable by any of the aforementioned methods, wherein the composition is preferably an immunogenic composition, in particular a vaccine.

A further aspect of the invention relates to the use of the immunogenic composition of the invention for the preparation of a medicament for treating or preventing SBV and/or treating or preventing viremia or malformations induced by SBV and/or preventing or reducing the transmission of SBV in an animal in need of said treatment.

Also, the invention provides a method of generating an immune response to SBV in an animal comprising administering to said animal the immunogenic composition of the invention.

In another aspect, the invention provides a method of treating or preventing SBV or treating or preventing viremia or malformations induced by SBV in an animal in need of said treatment, comprising administering to said animal a therapeutically effective amount of the vaccine composition of the invention.

The invention further provides a method for inducing an immune response against SBV and/or preventing or reducing viremia or malformations induced by SBV and/or preventing or reducing the transmission of SBV in an animal or a herd of animals comprising the step of administering the immunogenic composition of the invention to an animal in need thereof.

In the aforementioned methods, the immunogenic composition of the invention or the vaccine of the invention, respectively, is preferably administered in a single dose or more preferably in two doses.

EXAMPLE 1

Details about First SBV Isolation

BHK-21 cells have been extensively used for growth of Orthobyniaviruses. Following this, SBV virus was successfully isolated for the first time using this cell line, by FLI researchers in November 2011. Except for the BHK, *Culicoides variipennis* larvae cells (referred to as KC cells from Collection of Cell Lines in Veterinary Medicine, Friedrich-Loeffler-Institut, Greifswald-Insel Riems, Germany) were used. KC cells were incubated for 10 days with ultrasonically disrupted blood diluted in Schneider's media. The cells were then lysed by freezing and thawing. A monolayer of baby hamster kidney-21 cells (BHK, clone 13) was inoculated with the lysate. The inoculums was removed after 1 hour and replaced by Eagle minimal essential medium (EMEM). A strong cytopathic effect was visible after 5 days, and the culture supernatant tested positive for the novel virus, with a Cq value of approximately 14 in the specific cRT-qPCR (isolate 2) and $3\times10^6$ TCID50 per ml.

Manufacturing Process: General Description

The manufacturing process, as described below, is carried out following standard manufacturing methods, e.g. under conditions of sterility and after verification of correct operation conditions such as air filtration.

Description of Manufacturing Process:

1. Production of MSV (Master Stock Virus)

The SBV isolate 2 was used for MSV (Master Stock Virus) production. Roller bottle plated with BHK-21 cells ($5\times10^7$ cells) were infected at moi 0.0001. After 54 h of incubation roller bottle is frozen at −20, thawed and centrifugated at 2000 g for 5 min. Supernatant was collected and aliquots of 1 ml were stored at −80 C until further process.

2. Production of SBV Antigen

The BHK-21 cells (working cell stock—WCS) are stored frozen in liquid nitrogen. WCS was thawed and expanded on cell culture flasks (T160 $cm^2$) using EMEM media and 10% gamma irradiated FCS. Cells were trypsinised using recombinant (non animal origin) trypsin. One T160 flask was trypsinied and resuspended in 150 ml of EMEM media containing 2% FCS. This cell suspension was used to seed one roller bottle (495 $cm^2$). Roller bottles containing cell suspension were placed in 37 C incubator and roller at 0.5 rpm. Twelve to 16 h post plating cells were plated at density $5\times10^7$ per bottle. Infection using moi 0.0001 was used. Cells were continuously incubated at 37 C and rolled at 0.5 rpm for 50-56 h until specific SBV cytopathic effect (CPE) don't reach about 60-70% of cells. At this time point the complete roller bottle flasks were frozen at −20 C and thawed in 37 C water bath and stored at −80 C until further process.

The virus titration is performed following procedure:

Materials needed

1. BHK-21 cells (clone 13)
2. T75 flasks
3. Flat bottom 96 wells plates
4. Flat bottom 48 wells plates
5. Thermo 8-channel matrix pipette+tips
6. Eppendorf 8-channel pipette 50-1250+tips
7. Reservoir for multichannel pipettes
8. Trypisn+edta
9. Media ZB5
10. Pipettes 5, 10 and 25 ml 11. Pipetboy
12. Inverted microscope Procedure Highly confluent T75 flask trypsinize and cells nicely resuspend in 20 ml of media (10% FCS).

Add 100 ml of media (0% FCS) and mix well

This cell suspension pours into reservoir for multichannel pipettes

Use multichannel pipette to fill 100 μl of cell suspension into the wells of first 8 collumns of 96 wells plates Leave plates at 37° C. in CO2 incubator for 6-12 h to attach After this time prepare 48 wells plate and fill 1080 μl of serum free media in each well In the wells of the first column inoculate 120 μl of material for titration Using eppendorf 8-channel pipette with the program P/M (pipette 120 μl and mix 620 μl four times) firstly mix the first column where the material is inoculated Discard tips From the wells of the first column (with the new tips) pipette 120 μl into second and mix Discard tips Repeat this process until you finish the last column Using matrix pipette aspirate 800 μl from the first row of 48 well plate (which contains serial dilutions of one sample)

When attaching tips press firmly, but not too strong as the matrix function will not work Dispense 100 μl in 8 rows of 96 wells plate Incubate at 37 C for period of 3-4 days Read results on inverted microscope 3. Vaccine Formulations 3.1 Inactivation Procedure The process of inactivation of the final antigen lasts for a total of 72 hours, and the concentration of BEI used is 15 mM. Final antigen is inactivated by adding BEI 0.1 M at a proportion of 100 ml per liter of antigen being inactivated (final concentration 10 mM). After the addition of the BEI the mixture is homogenized for at least 15 minutes and the pH is verified. After the homogenization process, the mixture is decanted into a sterile container where it is kept in agitation, at 37+/−1° C., for 24 hours. After 24 hours, a second inactivation of the final antigen is carried out by means of adding BEI 0.1 M at a proportion of 50 ml per liter of antigen being inactivated (final concentration 5 mM). After the second addition of BEI, the process is repeated under the same conditions as described above for the first addition, but maintaining the mixture in agitation for 48 hours.

3.2 Neutralization of Residual BEI

Once the inactivation process has been completed, 1 M sodium thiosulphate solution is added at the proportion of 5 ml per liter of inactivated antigen (final concentration 5 mM), in order to neutralize the BEI. After the mixture has been homogenized, the pH is verified. If necessary, an adjustment is done with hydrochloric acid, to obtain a pH of 7.2+−0.2.

3.3 Adjuvants

Alhydrogel (aluminium hydroxide) and Quil-A (saponin) are used as adjuvants.

4. Proof of Concept Experiment in Cattle.

Eighteen (18)—7 month old cattle are used for the experiment. Animals are been divided into four groups with four animals in each group, while other two animals are used as contact controls. All animals are SBV sero-negative at the beginning of experiment. First group (of four animals) is vaccinated with the vaccine dose containing $10^6$ SBV TCID50/ml, the second with $10^5$ SBV TCID50/ml, third with $10^4$ SBV TCID50/ml and finally fourth group is not vaccinated as well as two animals within contact control. Within each group 4 animals are vaccinated by the subcutaneous route (2 mL) and revaccinated 3 weeks later. All animals in the study are challenged two weeks after revaccination (challenge dose=$10^7$ TCID50 of live virus/animal) except of contact control animals. All non-vaccinated animals develop viremia upon SBV challenge, staring at 3 dpi (days post infection) and lasting 2-3 days. Animals vaccinated show significantly lower viremia and reduced to no clinical symptoms compared to non-vaccinated animals after the SBV challenge.

EXAMPLE 2

1. Introduction

In this study, several inactivated vaccine formulations have been produced and subsequently tested in sheep and cattle regarding their ability to induce neutralizing antibodies and to prevent viraemia after experimental challenge infection.

2. Materials and Methods

Vaccines

Five different prototype vaccine formulations were produced (Table 1); all of them were inactivated SBV preparations in aqueous solution. SBV was either grown on two different baby hamster kidney (BHK-21) cell lines (vaccines “BHKCT-HT”, “BHK13-HT”, “BHK13-LT”) or on MA-104 cells (vaccines “MA-HT” and “MA-LT”).

The antigen-concentration was formulated using the infectious titre of SBV before inactivation with binary ethylenimine (BEI) using either a long (using 10 mM of BEI for 72 hours at 37° C.) or a short (using 2 mM of BEI for 12 hours at 37° C.) protocol.

Vaccine candidates contained antigen concentration as follows: 6.1 log 10 50% tissue culture infectious doses per ml ($TCID_{50}$/ml) (MA-HT) or 5.7 log 10 $TCID_{50}$/ml (BHKCT-HT, BHK13-HT, MA-LT) or 4.7 log 10 $TCID_{50}$/ml (BHK13-LT). Saponin and aluminium hydroxide were used as adjuvants (0.125 μg Saponin per 1 ml and 6.65 mg aluminium hydroxide per ml in all vaccine candidate formulations). All formulations were tested for the absence of bacterial contamination and in duplicates for successful inactivation by two subsequent passages in BHK-21 cells. The pH values of each prototype vaccine were adjusted at 6.8-7.2 at 20° C. The vaccines were kept at 4° C. until use.

TABLE 1

| Vaccines and animal groups. | | | | | |
|---|---|---|---|---|---|
| Vaccines Name | Cell line | Infectious titre used | Inactivation | Animals Animal group | Animal number |
| BHKCT-HT | BHK-21 clone CT | 5.7 log10 $TCID_{50}$/ml | long protocol | A (sheep) | S01-S05 |
| | | | | G (cattle) | C01-C06 |
| BHK13-HT | BHK-21 clone 13 | 5.7 log10 $TCID_{50}$/ml | short protocol | B (sheep) | S06-S10 |
| BHK13-LT | BHK-21 clone 13 | 4.7 log10 $TCID_{50}$/ml | short protocol | C (sheep) | S11-S15 |
| MA-HT | MA-104 | 6.1 log10 $TCID_{50}$/ml | short protocol | D (sheep) | S16-S20 |
| | | | | H (cattle) | C07-C10 |
| MA-LT | MA-104 | 5.7 log10 $TCID_{50}$/ml | long protocol | E (sheep) | S21-S25 |
| | | | | I (cattle) | C11-C16 |
| unvaccinated control | | | | F (sheep) | S26-S30 |
| | | | | K (cattle) | C17-C22 |

Animals

Twenty-five SBV-naive sheep of European domestic breeds (7-9 months of age) were assigned to 5 groups of 5 animals each, which were immunized subcutaneously with one of the prototype vaccines (see table 1). Another 5 sheep were kept as unvaccinated controls. Male and female animals were distributed equally.

In addition, 22 SBV antibody-negative female Holstein-Friesian cattle were assigned to four groups of four (group H) or six animals (groups G, I and K) each. Animals in group G, H and I were immunized subcutaneously with vaccines BHKCT-HT, MA-HT and MA-LT, respectively. Cattle in group K were kept as unvaccinated controls. On the day of the first vaccination, the animals were between 8 and 12 months of age.

In each case, the animals were vaccinated twice three weeks apart and three weeks after the second vaccination both vaccinated and control animals were inoculated with 2×0.5 ml of an SBV field strain that was only passaged in the natural host. During the entire study, rectal body temperatures were measured daily, and the animals were examined for clinical signs by veterinarians.

Sampling, Real-Time RT-PCR and Serology

Following the first vaccination, serum samples were collected at days 0, 3, 4, 7 and weekly thereafter. After the second vaccination, serum samples were taken in weekly intervals. Following challenge infection, serum samples were taken daily during the first eight days and on days 14 and 21. Samples of spleen, tonsils, and mesenteric and mandibular lymph nodes were taken at autopsy on days 22-29 after challenge infection and homogenized in 1 ml MEM.

RNA from serum and tissue samples taken at autopsy was extracted using the MagAttract Virus Mini M48 Kit for automated extraction (Qiagen, Germany) according to the manufacturer's recommendations. SBV genome loads were determined by a reverse transcription real-time PCR (RT-qPCR) (7) with an external standard based on the S genome segment. Furthermore, serum samples were analyzed with a commercially available SBV antibody ELISA (ID Screen® Schmallenberg virus Indirect, IDvet, France) using the recommended cut-off of 70% relative optical density compared to the positive control, and in a standard micro-neutralization assay.

3. Results

Clinical Observations and Post-Mortem Examinations

Following the first vaccination with the vaccine prototypes no adverse side effects were observed; none of the animals showed fever or any other clinical sign. After the second vaccination one cattle immunized with vaccine MA-HT (group H) developed a low-grade swelling at the injection site for 2 days.

After the challenge infection, one unvaccinated cattle developed fever on day 3, another showed mild diarrhea for three days. One animal out of group I had nasal discharge for one day.

Autopsy of the animals did not reveal any significant gross lesions. The mesenteric lymph nodes of all but one (S30) unvaccinated animals were PCR-positive; on average 2.86E+03 genome copies per mg (copies/mg) were detected. In addition, SBV RNA was found in the mandibular lymph nodes of 3 out of 5 unvaccinated sheep (S27-S29) and of all control cattle (average 2.68E+01 copies/mg), the tonsils of S27-S29 and C18-C20 (average 9.90E+01 copies/mg), and spleens of 4 out of 5 unvaccinated sheep (S26-S29; average 4.57E+03 copies/mg) and of two control calves (C17, C21; average 1.40E+01 copies/mg). No viral RNA was detected in any of the vaccinated animals.

Antibody Response

On the day of the first vaccination, all animals were negative in both serological assays.

Before challenge infection, no antibodies could be detected in the unvaccinated animals. Three weeks after infection all but one (S30) control sheep and cattle scored positive in the neutralization assay. Antibodies were found in cattle and in 2 out of the 5 unvaccinated sheep (S26, S29) by ELISA as well. Despite an increasing sample OD relative to the positive control OD value (S/P) both the control sheep S27 and S28 scored negative in the ELISA.

Three weeks after the first immunization with vaccine BHKCT-HT, BHK13-HT or BHK13-LT (SBV grown on BHK cells), all sheep and cattle were negative in the ELISA, while in S07, S08, S10 (BHKCT-HT), and S04 (BHK13-HT) low antibody titres were detected in the neutralization assay. Following the second vaccination antibodies were detected in at least one serological assay, in most cases a considerable increase of neutralizing antibodies was seen. Three weeks after challenge infection 8 out of 15 sheep (S04, S06, S07, S09, S10, S11, S12, S15) and 5 out of 6 cattle (C01-C05) were positive in both assays, 7 sheep (S01-S03, S05, S08, S13, S14) and the remaining cattle (C6) were positive in the neutralization test only, and S15 in the ELISA assay only.

After one immunization with vaccines MA-HT or MA-LT (SBV grown on MA-104 cells), all cattle and all but two sheep scored negative in both serological assays. S22 and S23 had titres of 1:5 and 1:7, respectively, in the neutralization assay. Following the second vaccination, in S19, S24, C08, and C14 no antibodies could be detected. S16, S21, C07, C09, and C10 scored positive in both serological assays, while the remaining animals were positive in the neutralization assay only. Three weeks after challenge infection all sheep of group D and 4 out of 5 sheep of group E were positive in the neutralization assay, in animal S16 antibodies could be detected by the ELISA, and animal S24 was negative in both assays. In all cattle of group H (high titre of SBV) antibodies were detectable by ELISA and neutralization assay. The same is true for C12 and C13 (group I, low SBV titre), C11, C15, and C16 scored positive only in the neutralization assay, and in C14 no antibodies could be detected by any test.

After the second immunization an increase of the average neutralizing antibody titers were observed, while after challenge infection, most of the neutralization titers remained constant in all vaccinated groups.

Real-Time RT-PCR

Following the first vaccination SBV genome was not detected in any animal (data not shown), confirming the successful inactivation of SBV with short and long BEI inactivation procedure.

After challenge infection, all but one (S30) unvaccinated sheep scored positive in the RT-qPCR between day 2 and 4 (S27-S29) or 5 (S26). In 1 out of 6 unvaccinated cattle (C19) SBV-genome was first detectable on day 1 after infection, the other 5 calves scored positive on day 2 for the first time. SBV genome remained detectable until day 5 (C17, C19-C21), 6 (C22) or 7 (C18). Three out of 6 cattle immunized with vaccine MA-LT (C12, C13, C16) were positive in the RT-qPCR on day 3, while the animals vaccinated with MA-HT vaccines did not develop RNAemia (RNA in the blood) upon challenge.

In serum samples taken from all vaccinated sheep, from control sheep S30, and from all cattle of groups G and H (high titer vaccine groups), viral RNA could not be detected following challenge infection.

4. Conclusion

Five different inactivated vaccine formulations have been developed and were subsequently tested in cattle and sheep. In the experiments none of the animals showed significant adverse effects and all of the animals seroconverted upon vaccination. Furthermore, majority but not all the animals developed detectable neutralizing SBV antibodies levels upon vaccination. Importantly, upon challenge infection, RNAemia was completely prevented by four prototype vaccines and considerably reduced by the fifth. Those data suggest that protection from virus infection is only partially mediated by neutralizing antibodies and that additional still undetermined mechanisms, most likely associated with cellular immunity, essentially contributed to virus clearance upon SBV challenge. The two major characteristics of inactivated vaccines are (i.) the complete inactivation of the infectious virus, which was demonstrated by cell culture passages and the missing RNAemia after the first immunization, and (ii.) the induction of protective immunity. Although neutralizing antibodies were not detected in every vaccinated animal prior to challenge infection, RNAemia was completely prevented by four prototype vaccines and considerably reduced by the fifth. The detection of viral RNA in the lymphoreticular system was used as diagnostic tool apart from RNAemia in the present study. In contrast to the controls all vaccinated animals were clearly negative for SBV-RNA in the lymphoid system (in the lymphoid organs at the time of autopsy) like the mesenteric lymph nodes. One of the unvaccinated control sheep showed neither RNAemia, nor RT-qPCR-positive tissue samples, nor seroconversion after challenge infection, the reason for that observation remains unclear. Possible explanations are a failed injection or a status of (natural) resistance to SBV infection.

Nevertheless, the absence of detectable RNA in most vaccine groups allows to draw the conclusion that, if even no viral genomes can be detected (in the serum), no challenge virus could be transmitted to the fetus.

Although RNAemia was prevented or markedly reduced by vaccination, antibodies were not detected in every animal prior to challenge infection in every test. Overall, the correlation of ELISA test and neutralization assay was greater in bovine than in ovine samples, especially after challenge infection of unvaccinated animal.

The highest levels of antibodies of all sheep groups were detected by neutralization test after challenge infection of unvaccinated sheep. The same was observed after immunization with several Rift Valley fever vaccines and subsequent challenge (8), where the applied vaccines, however, did not provide sterile immunity, but only a reduction of viraemia. As opposed to this, the SBV vaccine prototypes characterized in this study prevented RNAemia in sheep completely despite a low level of neutralizing antibodies.

In our study, the titre of neutralizing antibodies was influenced by the production cell line and the viral titre prior to inactivation. A dose dependence of the cell culture supernatant used for vaccine preparation was described for AKAV as well, independent whether inactivated or attenuated live vaccines were used (9; 10). At least 10^5.5 $TCID_{50}$/ml of virus were reported to be necessary for vaccine development. As 2 ml of a vaccine containing 6.1 log 10 $TCID_{50}$/ml virus grown on MA-104 cells prevented RNAemia completely, but in half of the calves which were immunized with 5.7 log 10 $TCID_{50}$/ml viral genome was detectable for one day, a similar minimal dose may be assumed for SBV. However, in vaccines produced on BHK-21-cells, the lower viral titre (5.7 log 10 TCID50/ml) prevented RNAemia completely in both animal species, in sheep merely 4.7 log 10 TCID50/ml were necessary.

In conclusion, in this proof-of-concept characterization of different vaccine candidates, a high efficacy could be demonstrated for four out of five SBV vaccine prototypes in both major target species. As a result, the development of a killed vaccine against Schmallenberg virus, which is efficacious and safe in cattle and sheep, is demonstrated. The results obtained in this study show that inactivated SBV vaccine can be successfully applied to support efforts for SBV spread control as well as disease prevention in domestic ruminants.

EXAMPLE 3

In the following, an alternative inactivation procedure and subsequent neutralization process is described, which also allowed the production (the further steps of production were performed in accordance with Example 1) of an effective vaccine for a successful prevention of infection with SBV:

Inactivation Procedure

The process of inactivation of the final antigen lasted for a total of 12 hours, and the concentration of BEI used was 2 mM. Final antigen was inactivated by adding BEI 0.17 M at a proportion of 11.9 ml per liter of antigen being inactivated (final concentration 2 mM). After the addition of the BEI, the mixture was kept in agitation, at 37+/−1° C., for 12 hours.

Neutralization of Residual BEI

Once the inactivation process has been completed, 1 M sodium thiosulphate solution was added at the proportion of 10 ml per liter of inactivated antigen (final concentration 10 mM), in order to neutralize the BEI.

EXAMPLE 4

Hereinafter, an alternative production of MSV (master stock virus) is described, which likewise enabled the manufacturing (the further steps of the manufacture process were performed in accordance with Example 1, wherein the inactivation procedure was done as described in Example 3) of an effective vaccine for a successful prevention of infection with SBV:

5. Production of MSV (Master Stock Virus)

The SBV isolate 2 was used for MSV (Master Stock Virus) production. Roller bottle plated with Ma104-Ak ($5\times10^7$ cells) were infected at moi 0.0001. After 54 h of incubation roller bottle is frozen at −20, thawed and centrifugated at 2000 g for 5 min. Supernatant was collected and aliquots of 1 ml were stored at −80 C until further process.

6. Production of SBV Antigen

The Ma104-Ak (working cell stock—WCS) are stored frozen in liquid nitrogen. WCS was thawed and expanded on cell culture flasks (T160 $cm^2$) using EMEM media and 10% gamma irradiated FCS. Cells were trypsinised using recombinant (non animal origin) trypsin. One T160 flask was trypsinized and resuspended in 150 ml of EMEM media containing 2% FCS. This cell suspension was used to seed one roller bottle (495 $cm^2$). Roller bottles containing cell suspension were placed in 37 C incubator and roller at 0.5 rpm. Twelve to 16 h post plating cells were plated at density $5\times10^7$ per bottle. Infection using moi 0.001 was used. Infected cells were continuously incubated at 37 C and rolled at 0.5 rpm for 72-96 h until specific SBV cytopathic effect (CPE) don't reach about 60-70% of cells. At this time point the complete roller bottle flasks were frozen at −20 C and thawed in 37 C water bath and stored at −80 C until further process.

IN THE SEQUENCE LISTING

SEQ ID NO:1 corresponds to the complete genomic sequence of a S segment of an infectious Schmallenberg virus (BH80/11-4), SEQ ID NO:2 corresponds to the complete genomic sequence of a M segment of an infectious Schmallenberg virus (BH80/11-4), SEQ ID NO:3 corresponds to the complete genomic sequence of a L segment of an infectious Schmallenberg virus (BH80/11-4), SEQ ID NO:4 corresponds to anti-parallel (i.e. complementary and inverse) RNA sequence of SEQ ID NO:1, SEQ ID NO:5 corresponds to the anti-parallel RNA sequence of SEQ ID NO:2, SEQ ID NO:6 corresponds to the anti-parallel RNA sequence of SEQ ID NO:3, SEQ ID NO: 7 corresponds to SEQ ID NO:1, wherein the nucleotide at position 9 is "a" instead of "g", and SEQ ID NO: 8 corresponds to the anti-parallel RNA sequence of SEQ ID NO:7 and thus corresponds to SEQ ID NO:4, wherein the nucleotide at position 831 is "u" instead of "c".

REFERENCES

All references cited herein are hereby entirely incorporated by reference.

1. B. Hoffmann., M. Scheuch, D. Höper, R. Jungblut, M. Holsteg, H. Schirrmeier, M. Eschbaumer, K. V. Goller, K. Wernike, M. Fischer, A. Breithaupt, T, C. Mettenleiter, M. Beer, Novel orthobunyavirus in Cattle, Europe, 2011. *Emerg. Infect. Dis.* 18, 469-472 (2012).
2. M.-M. Gariglinany et al., Schmallenberg virus in calf born at term with porencephaly, Belgium. *Emerg. Infect. Dis.* 18 (2012), doi: 10.3201/eid1806.120104.
3. M. D. Bowen et al., A reassortant bunyavirus isolated from acute hemorrhagic fever cases in Kenya and Somalia. *Virology.* 291, 185-190 (2001).
4. A. M. Q. King, M. J. Adams, E. B. Carstens, E. J. Lefkowitz, Eds., Virus Taxonomy: Ninth Report of the International Committee on Taxonomy of Viruses. (Elsevier, San Diego, USA, 2011), pp 725-731.
5. R. M. Kinney, C. H. Calisher, Antigenic relationships among Simbu serogroup (Bunyaviridae) viruses. *Am. J. Trop. Med. Hyg.* 30, 1307-1318 (1981).
6. M. F. Saeed, L. Li, H. Wang, S. C. Weaver, A. D. Barrett, Phylogeny of the Simbu serogroup of the genus Bunyavirus. *J. Gen. Virol.* 82, 2173-2181 (2001).
7. Bilk S, Schulze C, Fischer M, Beer M, Hlinak A, Hoffmann B. Organ distribution of Schmallenberg virus RNA in malformed newborns. Veterinary microbiology 2012 Mar. 30.
8. Kortekaas J, Antonis A F, Kant J, Vloet R P, Vogel A, Oreshkova N, et al. Efficacy of three candidate Rift Valley fever vaccines in sheep. Vaccine 2012 May 14; 30(23): 3423-9.
9. Kurogi H, Inaba Y, Takahashi E, Sato K, Goto Y, Satoda K, et al. Development of inactivated vaccine for Akabane disease. National Institute of Animal Health quarterly 1978 Winter; 18(3-4):97-108.
10. Kurogi H, Inaba Y, Akashi H, Takahashi E, Sato K, Satoda K, et al. Immune response of various animals to Akabane disease live virus vaccine. National Institute of Animal Health quarterly 1979 Summer; 19(1-2):23-31.

What is claimed is:

1. A method of generating an immune response to SBV in an animal comprising administering to said animal an immunogenic composition comprising:

a. an aziridine compound-inactivated Schmallenberg virus (SBV) in an amount which is equivalent to a virus titer of at least about $10^4$ $TCID_{50}$/mL per dose, wherein the inactivated SBV comprises a medium (M) RNA segment having a sequence that is inverse complementary to a nucleic acid sequence having at least 95% sequence identity with the nucleic acid sequence of SEQ ID NO:2 over the whole length of SEQ ID NO:2; and b. the aziridine compound binary ethyleneimine (BEI) neutralized with sodium thiosulphate wherein the immunogenic composition further comprises aluminum hydroxide and saponin.

2. The method according to claim 1, wherein the immunogenic composition is administered in a single dose or in two doses.

3. The method according to claim 1, wherein the immunogenic composition further contains one or more pharmaceutically acceptable carriers or excipients.

4. The method according to claim 1, wherein said one or more pharmaceutically acceptable carriers or excipients are selected from the group consisting of solvents, dispersion media, adjuvants, stabilizing agents, diluents, preservatives, antibacterial and antifungal agents, isotonic agents, and adsorption delaying agents.

5. A method of inducing an immune response against SBV in a herd of animals comprising comprising the step of administering an immunogenic composition comprising:

a. an aziridine compound-inactivated Schmallenberg virus (SBV) in an amount which is equivalent to a virus titer of at least about $10^4$ TCIDso/mL per dose, wherein the inactivated SBV comprises a medium (M) RNA segment having a sequence that is inverse complementary to a nucleic acid sequence having at least 95% sequence identity with the nucleic acid sequence of SEQ ID NO:2 over the whole length of SEQ ID NO:2; and b. the aziridine compound binary ethyleneimine (BEI) neutralized with sodium thiosulphate, wherein the immunogenic composition further comprises aluminum hydroxide and saponin.

6. The method according to claim 5, wherein the immunogenic composition is administered in a single dose or in two doses.

7. The method according to claim 5, wherein the immunogenic composition further contains one or more pharmaceutically acceptable carriers or excipients.

8. The method according to claim 7, wherein said one or more pharmaceutically acceptable carriers or excipients are selected from the group consisting of solvents, dispersion media, adjuvants, stabilizing agents, diluents, preservatives, antibacterial and antifungal agents, isotonic agents, and adsorption delaying agents.

* * * * *

SEQUENCE LISTING

```
<160> NUMBER OF SEQ ID NOS: 8

<210> SEQ ID NO 1
<211> LENGTH: 839
<212> TYPE: DNA
<213> ORGANISM: Schmallenberg virus
```

-continued

<400> SEQUENCE: 1

```
agtagtgagc tccactatta actacagaaa tatgtcaagc caattcattt ttgaagatgt     60
accacaacgg aatgcagcta catttaaccc ggaggtcggg tatgtggcat ttattggtaa    120
gtatgggcaa caactcaact tcggtgttgc tagagtcttc ttcctcaacc agaagaaggc    180
caagatggtc ctacataaga cggcacaacc aagtgtcgat cttacttttg gtggggtcaa    240
atttacagtg gttaataacc attttcccca atatgtctca aatcctgtgc cagacaatgc    300
cattacactt cacaggatgt caggatatct agcacgttgg attgctgata catgcaaggc    360
tagtgtcctc aaactagctg aagctagtgc tcagattgtc atgccccttg ctgaggttaa    420
gggatgcacc tgggccgatg gttatacaat gtatcttgga tttgcacctg gggccgaaat    480
gttccttgat gcttttgact tctatccact agttattgaa atgcataggg tcctcaagga    540
caatatggat gtaaatttta tgaaaaaagt cctccgccaa cgctatggaa caatgactgc    600
tgaagaatgg atgactcaga aaataacaga aataaaagct gcttttaatt ctgttggaca    660
gcttgcctgg gccaaatctg gattctctcc tgctgctaga accttcttgc agcaattcgg    720
tatcaacatc taaacctctt catcacagat cttcaatttc cgtgcaatat gtctatgtat    780
tgcacaccat tatactgcaa ggcttctgtt aagatagtta ataagtggag aacactact     839
```

<210> SEQ ID NO 2
<211> LENGTH: 4373
<212> TYPE: DNA
<213> ORGANISM: Schmallenberg virus

<400> SEQUENCE: 2

```
agtagtgaac taccacaatc aaaatgcttc tcaacattgt cttgatatct aacttagcct     60
gtttagcttt tgcactccca cttaaggaag gcactagagg gtctaggtgc ttcctgaatg    120
gcgaactggt taaaactgtt aacacatcaa aggtcgtttc agaatgctgt gtgaaagacg    180
acatatctat cattaaatca aatgctgaac attataaatc aggagatcgg ttggctgctg    240
taataaaata ttatcgttta tatcaggtga aggattggca ttcttgcaat ccaatttatg    300
atgaccacgg ttcctttatg atattagata tagataatac tggcacatta atccctaaaa    360
tgcatacatg cagagttgaa tgcgaaatag cactgaataa agatactggc gaagttatat    420
tgaattcata tcgaattaac cactaccgaa tctcgggcac aatgcatgta tcaggttggt    480
ttaaaaacaa aattgagatt cctttggaaa acacatgcga atccattgag gtaacatgtg    540
gattaaaaac acttaatttt catgcatgtt tccataccca taagtcatgc acccgctatt    600
ttaaaggatc aatcctgccg gaattgatga tcgaatcatt ttgtacgaat cttgaattaa    660
tactgctagt aactttcata ttagttgggt ctgtcatgat gatgatattg acgaaaacat    720
atatagtata tgtgttcatt cctatatttt atccatttgt gaaattatat gcttatatgt    780
acaacaaata ttttaaattg tgtaaaaatt gcctgttagc agtacatccc tttacaaatt    840
gcccatcgac atgcatctgt ggaatgattt acactaccac tgaatcactc aaattgcatc    900
gcatgtgtaa caattgttct ggctataaag cattgccgaa aacaaggaaa ttgtgtaaaa    960
gtaaaatatc caatatagtg ctatgtgtga taacatcact gatatttttc tcatttatca   1020
cacctatatc gagtcaatgt atcgatatag aaaaactgcc agacgagtat attacatgta   1080
aaagagagct agctaatatc aaaagcttga caattgatga cacatatagc tttatatatt   1140
cctgtacatg cataattgtg ttaatattac ttaaaaaggc agcaaagtat atcttgtact   1200
gcaactgcag cttttgtggt atggtacatg aacgacgtgg attgaagata atggacaact   1260
```

-continued

```
ttacaaacaa gtgcctaagt tgtgtatgcg cagaaaacaa gggcttaaca attcacagag   1320
cctctgagaa atgtctgttc aaatttgaat caagttataa taggaccggg ttgataatct   1380
ttatgcttct gttagtccca acaattgtaa tgacgcaaga aactagtatt aactgcaaaa   1440
acattcaatc aactcagctt acaatagagc acctgagtaa gtgcatggca ttttatcaaa   1500
ataaaacaag ctcaccagtt gtaatcaatg aaataatttc agatgcttca gtagacgaac   1560
aagaattaat aaaaagttta aacttgaact gtaatgtcat agataggttt atttccgaat   1620
ctagtgttat tgagactcaa gtttattatg agtatataaa atcacagttg tgccctctcc   1680
aagtgcatga tattttcact atcaattcag caagtaacat acaatggaaa gcactggccc   1740
gaagtttcac cttaggagtg tgcaatacga atcctcataa acatatatgt agatgcttgg   1800
agtctatgca aatgtgcaca tcaaccaaga cagaccacgc tagggaaatg tcaatatatt   1860
atgatggtca tccagatcgc tttgagcatg acatgaaaat aatattgaat ataatgagat   1920
atatagtccc tggattaggt cgagtcttgc ttgatcaaat caaacaaaca aaagactacc   1980
aagctttacg ccacatacaa ggtaagcttt ctcctaaatc gcagtcaaat ttacaactta   2040
aaggatttct ggaatttgtt gattttatcc ttggtgcaaa cgtgacaata gaaaaaaccc   2100
ctcaaacatt aactacatta tctttgataa aaggagccca cagaaacttg gatcaaaaag   2160
atccaggtcc aacaccaata ctggtatgca aatcaccaca aaaagtggta tgctactcac   2220
cacgtggtgt cacacaccca ggagattata tatcatgcaa atctaagatg tataagtggc   2280
catctttagg ggtatacaaa cataatagag accagcaaca agcctgcagc agtgacacac   2340
attgcctaga gatgtttgaa ccagcagaaa gaacaataac tacaaaaata tgcaaagtaa   2400
gtgatatgac ttattcagaa tcgccatata gtactggaat accatcatgc aacgtgaaga   2460
gatttggatc atgtaatgta aggggtcatc aatggcaaat tgcagaatgc tcaaatggct   2520
tattttacta tgtttcagct aaagcccatt cgaaaactaa cgatataaca ctgtactgtt   2580
tatcagcaaa ttgcctggac ttgcgttatg cattcagatc cagtagttgt tcagatatag   2640
tatgggatac aagttatcga aataaattaa cacctaaatc tattaatcat ccagatattg   2700
aaaactacat agcagcgctt cagtcagata ttgcaaatga tttaactatg cactacttta   2760
aaccattaaa aaaccttcca gcaataattc ctcaatacaa aacaatgaca ttgaatgggg   2820
acaaggtatc aaatggtatt agaaatagtt atatcgagtc gcacatccct gcaattaatg   2880
gtttatcagc agggattaat attgccatgc caaatggaga aagcctcttt tccattatta   2940
tctatgtcag aagagtaata aataaagcat cgtatcgatt tctatatgaa acaggaccca   3000
caattggaat aaatgccaag cacgaagagg tatgtaccgg gaagtgccca agcccaatac   3060
cacatcaaga tggttgggtc acattctcaa aggaaagatc aagtaattgg ggctgtgaag   3120
aatggggttg cttggcaata aatgatggtt gtttatatgg gtcatgtcaa gacataataa   3180
ggcctgaata taagatatac aagaagtcta gtattgaaca aaaggatgtt gaagtttgta   3240
taaccatggc ccatgaatca ttctgcagta ccgttgatgt tctccaacct ttaattagcg   3300
acaggataca attagatatc caaacgattc aaatggactc tatgccaaat ataattgcag   3360
tcaagaatgg gaaagtttat gttggagata tcaatgactt aggttcgaca gcaaagaaat   3420
gtggctcagt ccaattatat tctgaaggga tcattggatc gggaacccca aaatttgatt   3480
atgtttgcca tgcattcaat cgtaaagatg tcatccttcg aagatgcttt gataactcat   3540
atcagtcttg tcttctcttg gaacaagata atacattaac tattgcttct accagtcata   3600
```

tggaagtgca taaaaaagtt tcaagcgtgg gtacaatcaa ttataaaatt atgttagggg 3660
attttgacta caatgcatat tcaacacaag caacagtcac aatagatgag atcaggtgtg 3720
gtggttgtta tggctgccct gaaggaatgg cttgcgcact caaattgagt accaatacca 3780
tcgggagttg ttcaataaaa agtaactgcg atacatacat taaaataata gcagtcgatc 3840
cgatgcagag cgagtattcc attaagttaa actgcccact agcaacagag acagtttcag 3900
taagtgtgtg ctcagcttct gcttacacaa aaccttcaat atctaaaaat caaccaaaaa 3960
ttgttttgaa ttccttagat gaaacatctt acatcgagca acatgataaa aagtgttcta 4020
catggctttg cagagtttat aaagaaggga ttagcgtaat atttcagcct ctatttggca 4080
acctatcttt ctattggaga ctgacaatat atataataat ctctttgatt atgctaattc 4140
tgtttctata catattaata ccactgtgca aacggctaaa aggtttattg gaatacaatg 4200
agagaatata ccaaatggaa aataaattta agtgataagc cttataacaa tgagcaatta 4260
taaatgaata aataaaaaca ataaaagata aacaaataac aacatatata tgtggttaca 4320
catatatatg taattattca gctgagaagt ttttcatgtg gtagaacact act 4373

<210> SEQ ID NO 3
<211> LENGTH: 6882
<212> TYPE: DNA
<213> ORGANISM: Schmallenberg virus

<400> SEQUENCE: 3
agtagtgtac ccctaattac aatcactatg gagacataca agattaacat ttttagagat 60
aggatcaacc agtgtcgaag tgctgaagaa gccaaagaca ttgttgctga tcttctcatg 120
gctagacatg actactttgg tagagaggta tgttattacc tggatatcga attccggcag 180
gatgttccag cttacgacat acttcttgaa tttctgccag ctggcactgc tttcaacatt 240
cgcaattgta caccagacaa ttttatcatt cacaatggca agctttatat cattgactat 300
aaagtatcaa ctgatcatgc atatggtcaa aaaacttatg aaaagtacac ccagatcttt 360
ggagacgcat tgtcagaatt gccgtttgat tttgaagttg tgatcatccg tgctgaccct 420
ctgcgagata ctatccatgt taattcaaat caattcttgg aaatatttgg gccgctcaac 480
ataaaccttg attttacttg gttctttaat ttgcgatccc tgatatatga gaaatataag 540
gatgacgaca gattcctaga aattgtgaat caaggtgaat ttacgatgac tggaccctgg 600
attgatgagg ataccccgga gctctattca caccctgtct tttggaatt ctatgattct 660 ttagatgaga tggctaaact gacattccat gagtctatga catttgatgc aactcgcggt 720
gagaaatgga atcaaaatct acaaaaggtt ataaatagat atggcaatga ttataacatt 780
tttgtgaaag aggccgctgc aggaatcttt agatgtgaag ggaactaccc aaaaccaaat 840
catgatgaaa tcacaatcgg ttggaatcaa atggttcaaa gagtgagtac tgagagaaac 900
ctgactcaag atgtcagcaa gcaaaaacca tctattcatt tcatatgggg tcaacctgac 960
gaaacatcaa atgcgacaac accaaaacta atcaagattg caaaagcact ccaaaatatt 1020
tctggcgagt ctacatatat aagcgcattc agagcattgg gtatgcttat ggacttttct 1080
gagaacacag ctttatatga agcacacact agcaaactaa aaagtatggc aagacagaca 1140
tcgaaaagaa ttgatactaa actggaacca atcaaaatag gcacggcgac aatttattgg 1200
gaacagcagt ttaaactgga tactgaaata atgaatacaa aagacaaatc acatttgcta 1260
aaagattttc ttggcatagg gggtcacgtg caattttcaa aaaagaccat tgacgatttg 1320
gatactgaca aacctactat attagatttc aacaaaaagg aagtcattga tttttgcaaa 1380

-continued

```
ttccagtatg aaaatgtaaa gaaaatacta tccggagata ataatctaga gcgtatagga   1440
tgttatttag aagaatatgg tgcaaatatt gcatcatgtt caaaggatac atgggatcag   1500
attaaccaga tagggaagtc aaattactgg gcttgtatta aagatttttc agtcttgatg   1560
aaaaatatgt tggcagtttc tcaatataat aggcacaata cttttcgtgt agtgtgttgt   1620
gcaaacaata atctgtttgg gtttgtaatg ccttcttctg atattaaagc aaagcgatcc   1680
acacttgttt acttcttagc tgtgttgcat tctactcctc agaatgtgat gcaccacggt   1740
gcattgcatg cgacatttaa aactggttca aaatacctta gtatctctaa aggaatgcgt   1800
ttagataaag aacgatgtca acgcatagtt agttcaccgg gactttttat gttgactaca   1860
ttgatgtttg caggagacaa tccgacactc aatttgactg atgtcatgaa ttttacattc   1920
cacacttccc tgtctataac caaagctatg ctgtcattga cagaaccatc aagatatatg   1980
ataatgaatt cattagccat atccagtcat gttagagatt atatagcaga aaaatttggc   2040
ccttatacaa agaccagctt ctctgtagta atggcaaact tgattaaaag gggatgttat   2100
atggcatata atcaaagaga taaagtagac atgaggaata tctgcctaac agattatgaa   2160
ataactcaaa aaggtgtgag agataacaga gacctatcat caatctggtt tgaaggctat   2220
gtatcactaa aagaatatat taaccaaata tatctaccat tttacttcaa ttcaaaaggt   2280
ttgcatgaaa agcatcatgt tatgatagat ctggctaaga caatcttaga tatagaaagg   2340
gaccagagat taaatatccc aggaatatgg tctacaacac ctagaaaaca aactgcaaat   2400
ttaaatataa ctatctatgc agttgcaaaa aatctaataa tggacactgc tagacataat   2460
tatattagat cacggataga aaacacaaac aacttaaata gatcgatatg cactatttct   2520
acattcacca gctctaaatc atgtattaaa gtaggcgact ttgagaaaga aaaaagctca   2580
gcaacaaaaa aggctgcaga ttgcatgtca aaagagataa agaagtatac aattgcaaac   2640
ccagaatttg ttgatgaaga gttactaaat gcaactataa gacattcacg ctatgaagac   2700
ttaaaaaaag caatcccgaa ttatattgac attatgtcaa ctaaagtatt tgattctctg   2760
taccagaaaa taaaaaggaa ggagatagat gataaaccca ctgtgtatca tatactctct   2820
gctatgaaga atcacacaga ttttaagttt acattcttta acaaaggcca aaaaacagca   2880
aaggataggg aaatattcgt aggcgaattt gaggcaaaaa tgtgcttgta tttagtggag   2940
aggatatcta aagaacgctg taagttgaat ccagatgaga tgattagtga accaggcgat   3000
tctaaattga aaaaattaga agagcttgca gagtctgaaa tacgattcac agcagcaact   3060
atgaaacaga tcaaagaacg ctatttagca gaaatgggag aagcaagcca tatgatcgca   3120
tataaaccac attctgttaa gattgaaatc aatgcagaca tgtcaaaatg gagtgcccaa   3180
gatgttttat tcaaatattt ctggttgttt gcattagatc ccgcacttta tctgcaagaa   3240
aaagaaagga tattgtactt cctatgcaat tatatgcaaa aaaagctaat tctgcctgat   3300
gaaatgctct gtagcatcct tgaccaacgt atcaaacatg aggatgatat aatatatgaa   3360
atgaccaatg gcttatcgca aaattgggtc aatattaaac ggaactggct gcaggggaat   3420
ctcaattaca caagtagcta cctacattca tgttctatga atgtttataa ggatattcta   3480
aagagagcag ccactttact agaaggggaa gttttagtca attctatggt tcattctgat   3540
gacaatcaca cttcaatagt gatgatccaa gataaattag atgatgatat tgttattgaa   3600
ttttctgcaa aactatttga aaaaatatgt ctaacttttg gaaatcaagc aaatatgaag   3660
aagacatata taacaaattt cataaaggag ttcgtttcac tttttaatat ttatggtgag   3720
```

-continued

```
ccattttctg tttatggtcg ctttattttg acatctgttg gcgattgtgc ttttcttgga   3780
ccatatgagg atgttgccag taggttgtct gcaacgcaga cagcaattaa gcatggagca   3840
cctccatcac ttgcatggac tgctattgca ttaactcagt ggataacaca tagcacatat   3900
aacatgcttc caggtcaaat caatgatcct acttcatctt tacctagtca tgatagattt   3960
gagctgccta tagaattgtg tggcttaata aattcagaat tacccactat agctatagca   4020
ggtttggaag cagataatct aagttattta gttaggttat caaaaagaat gtcccctata   4080
catctttgcc gtgaaccaat ccagcatcaa tatgagaata tacatacatg ggatataagt   4140
aaactgacac aatgtgatat tttcagactt aagcttttaa gatacatgac gttagactca   4200
actatgtcat ctgatgatgg aatgggcgaa actagtgaaa tgagatctag gtctcttctg   4260
acaccaagaa aattcactac tgcaagttcg ttatctagat tgcattcata tgctgattat   4320
caaaaaacaa tacaagacca acagaaaatt gaagaattat ttgaatattt tatagccaac   4380
cctcaactat tggttacaaa aggtgagact tgtgaagagt tctgtatgtc tgtattgttc   4440
agatacaaca gtcgtaaatt taaagaatca ttgtctattc aaaacccagc tcagctcttc   4500
atagaacaag tattgtttgc aaataaacca atgatagact atacaagtat tcatgatagg   4560
ttgtttggta tacaagatga cccaaatata aatgatgcta catgtattat tggcaagaag   4620
acttttgttg aaacatatca gcaaataaaa attgatgtag aaaaatttac acttgatgta   4680
gaggatataa agacgatata tagcttctgt ataatgaacg accctatatt agttgcttgt   4740
gcaaacaact tgttaatttc aatacaggga gtggagatgc aacgattggg tatgacatgc   4800
tgttatatgc cggagattaa gagccttaaa gtaatttatc atagtcctgc tctcgtatta   4860
cgtgcttatg taacagataa ctatgagcaa aaagggatgg agccagatga aatgcggaga   4920
gatatatatc atttagaaga atttatagag aagacaaaat tgaggacaaa tatgcaaggg   4980
agaattgcaa ataatgaaat taagttaatg aagcgagatt tgaaatttga agtgcaggaa   5040
ttgactaaat tctatcagat ctgttatgaa tatgtgaaat caacagaaca caaaattaaa   5100
atattcatcc ttccaaaaaa ggcttacact cccattgatt tctgctcatt agtaacaggt   5160
aatctgatat cagacaacaa atggatggtt gttcactatt taaaacaaat aactgtccca   5220
gcaaagaagg cacaaatagc cacatctata gatctggaaa tacaaatagc ctacgaatgt   5280
ttcaggctaa ttgcacattt tgctgatatg ttcctaaatg atgactccaa aaaagcttat   5340
attaatgcaa ttattaacac atatacatac aaggatgttc aagtatccag tctctacaag   5400
aaaatcaaaa attcgagact acgttcaaaa attataccat tattatatca cctgggcgat   5460
ttgcaacaaa tagacgttga cagatttgat gcagaaaaag cagaagagca gatcacatgg   5520
aataactggc aaacatctcg agaatttact actggtccaa ttgatctatc aatcaaaggt   5580
tatggacggt caataaggat cgtaggtgag gacaacaagc ttacagctgc agaaatgcaa   5640
ttgtcaagag tgagaagtga tatagtatca aggcatggac aggctttatt gaacaaacct   5700
catgggctaa aattagagaa aatggaacca gtgactgatc taaatcctaa attatggtat   5760
attgcatacc aattgcgtga gaaaaagcgg tatcactatg gggtctttag tacatcttat   5820
atagaagagc ataactcaag gatagaagca tctcggatac gtaagactaa taaatggata   5880
ccagtttgcc ctattgctat atcaaaacaa tcatctgatg gaaagcctag tcttgcaaaa   5940
atccctatgt taaatattgg ggagattaaa tttacaaaac tacagattgc agtagatgat   6000
catgcaatga ttaggaaagc cccatttagt aagatggtgt tctttgatgg cccacccata   6060
cagagcggtg gcattgacat tggaaagctt atgaagaacc aaaatattct caatttgagg   6120
```

ttagataata tacagagtat aacattatta gatttgtgcc gcatattttc atgccgaggg 6180
tctaaagtgg atcaagatgc atttgaattc ttatctgatg aacctttgga tgaagatgtt 6240
attgatgaat tagatagctc acctgcatta gtggtatctt acacaaagaa atcaaccaaa 6300
tccaatagtt tcaaaaatgt tatagttaga gcattgataa gagaatgtga tatatttgaa 6360
gatataatgg acataacaga cgatggattc acatctgata gcaatctaga ggtgttagaa 6420
aacttaacat ggattttaaa tatgctcgca acaaatcagt ggtctacaga actgttagca 6480
tgcatacaca tgtgtttata tcgcaatgag atggatcata tctatcacaa ttttcaagtt 6540
ccagaaatat ttgtcgacaa tccaatctca ttaaatgtaa agtgggatga agtaattatg 6600
ttcttaaaca tactgcgaga cagagattac aaatttgagc catgggtgtc tatactgaat 6660
cattccttaa ctaaagctat agagtatgct tacaaaaaga tggaagagga gaggaagcag 6720
aaatcaacag gcatcaacaa attcttaaag ggtaaaaaaa tgggtggcag atcaaagttt 6780
gatttccagt agcttgatct taaataatac ataatctttg ccccaaatct gtattatata 6840
aataattcta aagtagtttc atgtaattag gggcacacta ct 6882

<210> SEQ ID NO 4
<211> LENGTH: 839
<212> TYPE: RNA
<213> ORGANISM: Schmallenberg virus

<400> SEQUENCE: 4
aguaguguuc uccacuuauu aacuaucuua acagaagccu ugcaguauaa uggugugcaa 60
uacauagaca uauugcacgg aaauugaaga ucugugauga agagguuuag auguugauac 120
cgaauugcug caagaagguu cuagcagcag gagagaaucc agauuuggcc caggcaagcu 180
guccaacaga auuaaaagca gcuuuuauuu cuguuauuuu cugagucauc cauucuucag 240
cagucauugu uccauagcgu uggcggagga cuuuuuucau aaaauuuaca uccauauugu 300
ccuugaggac ccuaugcauu ucaauaacua guggauagaa gucaaaagca ucaaggaaca 360
uuucggcccc aggugcaaau ccaagauaca uuguauaacc aucggcccag gugcaucccu 420
uaaccucagc aaggggcaug acaaucugag cacuagcuuc agcuaguuug aggacacuag 480
ccuugcaugu aucagcaauc caacgugcua gauauccuga cauccuguga aguguaaugg 540
cauugucugg cacaggauuu gagacauauu ggggaaaaug guuauuaacc acuguaaauu 600
ugaccccacc aaaaguaaga ucgacacuug guugugccgu cuuauguagg accaucuugg 660
ccuucuucug guugaggaag aagacucuag caacaccgaa guugaguugu ugcccauacu 720
uaccaauaaa ugccacauac ccgaccuccg gguuaaaugu agcugcauuc cguuguggua 780
caucuucaaa aaugaauugg cuugacauau uucuguaguu aauaguggag cucacuacu 839

<210> SEQ ID NO 5
<211> LENGTH: 4373
<212> TYPE: RNA
<213> ORGANISM: Schmallenberg virus

<400> SEQUENCE: 5
aguaguguuc uaccacauga aaaacuucuc agcugaauaa uuacauauau auguguaacc 60
acauauauau guuguuauuu guuuaucuuu uauuguuuuu auuuauucau uuauaauugc 120
ucauuguuau aaggcuuauc acuuaaauuu auuuuccauu ugguauauuc ucucauugua 180
uuccaauaaa ccuuuuagcc guuugcacag ugguauuaau auguauagaa acagaauuag 240

-continued

```
cauaaucaaa gagauuauua uauauauugu cagucuccaa uagaaagaua gguugccaaa    300
uagaggcuga aauauuacgc uaaucccuuc uuuauaaacu cugcaaagcc auguagaaca    360
cuuuuuauca uguugcucga uguaagaugu uucaucuaag gaauucaaaa caauuuuugg    420
uugauuuuua gauauugaag guuuugugua agcagaagcu gagcacacac uuacugaaac    480
ugucucuguu gcuagugggc aguuuaacuu aauggaauac ucgcucugca ucggaucgac    540
ugcuauuauu uuaauguaug uaucgcaguu acuuuuuauu gaacaacucc cgaugguauu    600
gguacucaau uugagugcgc aagccauucc uucagggcag ccauaacaac caccacaccu    660
gaucucaucu auugugacug uugcuugugu ugaauaugca uuguagucaa aauccccuaa    720
cauaauuuua uaauugauug uacccacgcu ugaaacuuuu uuaugcacuu ccauaugacu    780
gguagaagca auaguuaaug uauuaucuug uuccaagaga agacaagacu gauaugaguu    840
aucaaagcau cuucgaagga ugacaucuuu acgauugaau gcauggcaaa cauaaucaaa    900
uuuuggggguu cccgauccaa ugaucccuuc agaauauaau uggacugagc cacauuucuu    960
ugcugucgaa ccuaagucau ugauaucucc aacauaaacu uucccauucu ugacugcaau   1020
uauauuuggc auagagucca uuugaaucgu uuggauaucu aauuguaucc ugucgcuaau   1080
uaaagguugg agaacaucaa cgguacugca gaaugauuca ugggccaugg uuauacaaac   1140
uucaacaucc uuuuguucaa uacuagacuu cuuguauauc uuauauucag gccuuauuau   1200
gucuugacau gacccauaua aacaaccauc auuuauugcc aagcaacccc auucuucaca   1260
gccccaauua cuugaucuuu ccuuugagaa ugugacccaa ccaucuugau gugguauugg   1320
gcuugggcac uucccgguac auaccucuuc gugcuuggca uuuauuccaa uugugggucc   1380
uguuucauau agaaaucgau acgaugcuuu auuuauuacu cuucugacau agauaauaau   1440
ggaaaagagg cuuucuccau uuggcauggc aauauuaauc ccugcugaua aaccauuaau   1500
ugcagggaug ugcgacucga uauaacuauu ucuaauacca uuugauaccu ugucccccauu   1560
caaugucauu guuuuguauu gaggaauuau ugcuggaagg uuuuuuaaug guuuaaagua   1620
gugcauaguu aaaucauuug caauaucuga cugaagcgcu gcuauguagu uuucaauauc   1680
uggaugauua auagauuuag guguuaauuu auuucgauaa cuuguauccc auacuauauc   1740
ugaacaacua cuggaucuga augcauaacg caaguccagg caauuugcug auaaacagua   1800
caguguuaua ucguuaguuu ucgaaugggc uuuagcugaa acauaguaaa auaagccauu   1860
ugagcauucu gcaauuugcc auugaugacc ccuuacauua caugauccaa aucucuucac   1920
guugcaugau gguauuccag uacuauaugg cgauucugaa uaagucauau cacuuacuuu   1980
gcauauuuuu guaguuauug uucuuucugc ugguucaaac aucucuaggc aaugugugucc   2040
acugcugcag gcuuguugcu ggucucuauu auguuuguau accccuaaag auggccacuu   2100
auacaucuua gauuugcaug auauauaauc uccugggugu gugacaccac guggugagua   2160
gcauaccacu uuuugugggug auuugcauac caguauuggu guuggaccug gaucuuuuug   2220
auccaaguuu cugugggcuc cuuuuaucaa agauaaaugua guuaauguuu gagggguuuu   2280
uucuauuguc acguuugcac caaggauaaa aucaacaaau uccagaaauc cuuuaaguug   2340
uaaauuugac ugcgauuuag gagaaagcuu accuuguaug uggcguaaag cuugguaguc   2400
uuuuguuugu uugauuugau caagcaagac ucgaccuaau ccagggacua uauaucucau   2460
uauauucaau auuauuuuca ugucaugcuc aaagcgaucu ggaugaccau cauaauauau   2520
ugacauuucc cuagcguggu cugucuuggu ugaugugcac auuugcauag acuccaagca   2580
ucuacauaua uguuuaugag gauucguauu gcacacuccu aaggugaaac uucgggccag   2640
```

-continued ugcuuuccau uguauguuac uugcugaauu gauagugaaa auaucaugca cuuggagagg 2700
gcacaacugu gauuuuauau acucauaaua aacuugaguc ucaauaacac uagauucgga 2760
aauaaaccua ucuaugacau uacaguucaa guuuaaacuu uuuauuaauu cuuguucguc 2820
uacugaagca ucugaaauua uuucauugau uacaacuggu gagcuuguuu uauuuugaua 2880
aaaugccaug cacuuacuca ggugcucuau uguaagcuga guugauugaa uguuuuugca 2940
guuaauacua guuucuugcg ucauuacaau uguugggacu aacagaagca uaaagauuau 3000
caacccgguc cuauuauaac uugauucaaa uuugaacaga cauuucucag aggcucugug 3060
aauuguuaag cccuuguuuu cugcgcauac acaacuuagg cacuuguuug uaaaguuguc 3120
cauuaucuuc aauccacguc guucauguac cauaccacaa aagcugcagu ugcaguacaa 3180
gauauacuuu gcugccuuuu uaaguaauau uaacacaauu augcauguac aggaauauau 3240
aaagcuauau gugucaucaa uugucaagcu uuugauauua gcuagcucuc uuuuacaugu 3300
aauauacucg ucuggcaguu uuucuauauc gauacauuga cucgauauag gugugauaaa 3360
ugagaaaaau aucagugaug uuaucacaca uagcacuaua uuggauauuu uacuuuuaca 3420
caauuuccuu guuuucggca augcuuuaua gccagaacaa uuguuacaca ugcgaugcaa 3480
uuugagugau ucaguggu ag uguaaaucau uccacagaug caugucgaug ggcaauuugu 3540
aaagggaugu acugcuaaca ggcaauuuuu acacaauuua aaauauuugu uguacauaua 3600
agcauauaau uucacaaaug gauaaaauau aggaaugaac acauauacua uauauguuuu 3660
cgucaauauc aucaucauga cagacccaac uaauaugaaa guuacuagca guauuaauuc 3720
aagauucgua caaaaugauu cgaucaucaa uuccggcagg auugauccuu uaaaauagcg 3780
ggugcaugac uuaugggu au ggaaacaugc augaaaauua aguguuuuua auccacaugu 3840
uaccucaaug gauucgcaug uguuuuccaa aggaaucuca auuuuguuuu uaaaccaacc 3900
ugauacaugc auugugcccg agauucggua gugguuaauu cgauaugaau ucaauauaac 3960
uucgccagua ucuuuauuca gugcuauuuc gcauucaacu cugcauguau gcauuuuagg 4020
gauuaaugug ccaguauuau cuauaucuaa uaucauaaag gaaccguggu caucauaaau 4080
uggauugcaa gaaugccaau ccuucaccug auauaaacga uaauauuuua uuacagcagc 4140
caaccgaucu ccugauuuau aauguucagc auuugauuua augauagaua ugucgucuuu 4200
cacacagcau ucugaaacga ccuuugaugu guuaacaguu uuaaccaguu cgccauucag 4260
gaagcaccua gacccucuag ugccuuccuu aagugggagu gcaaaagcua aacaggcuaa 4320
guuagauauc aagacaaugu ugagaagcau uuugauugug guaguucacu acu 4373

<210> SEQ ID NO 6
<211> LENGTH: 6882
<212> TYPE: RNA
<213> ORGANISM: Schmallenberg virus

<400> SEQUENCE: 6
aguagugugc cccuaauuac augaaacuac uuuagaauua uuuauauaau acagauuugg 60
ggcaaagauu auguauuauu uaagaucaag cuacuggaaa ucaaacuuug aucugccacc 120
cauuuuuuua cccuuuaaga auuuguugau gccuguugau uucugcuucc ucuccucuuc 180
caucuuuuug uaagcauacu cuauagcuuu aguuaaggaa ugauucagua uagacaccca 240
uggcucaaau uuguaaucuc ugucucgcag uauguuuaag aacauaauua cuucaucccca 300 cuuuacauuu aaugagauug gauugucgac aaauauuucu ggaacuugaa aauugugaua 360

-continued

```
gauaugaucc aucucauugc gauauaaaca cauguguaug caugcuaaca guucuguaga    420
ccacugauuu guugcgagca uauuuaaaau ccauguuaag uuuucuaaca ccucuagauu    480
gcuaucagau gugaauccau cgucuguuau guccauuaua ucuucaaaua uaucacauuc    540
ucuuaucaau gcucuaacua uaacauuuuu gaaacuauug gauuugguug auuucuuugu    600
guaagauacc acuaaugcag gugagcuauc uaauucauca auaacaucuu cauccaaagg    660
uucaucagau aagaauucaa augcaucuug auccacuuua gacccucggc augaaaauau    720
gcggcacaaa ucuaauaaug uuauacucug uauauuaucu aaccucaaau ugagaauauu    780
uugguucuuc auaagcuuuc caaugucaau gccaccgcuc uguaugggug ggccaucaaa    840
gaacaccauc uuacuaaaug gggcuuuccu aaucauugca ugaucaucua cugcaaucug    900
uaguuuugua aauuuaaucu ccccaauauu uaacauaggg auuuuugcaa gacuaggcuu    960
uccaucagau gauuguuuug auauagcaau agggcaaacu gguauccauu uauuagucuu   1020
acguauccga gaugcuucua uccuugaguu augcucuucu auauaagaug uacuaaagac   1080
cccauaguga uaccgcuuuu ucucacgcaa uugguaugca auauaccaua auuuaggauu   1140
uagaucaguc acugguucca uuuucucuaa uuuuagccca ugagguuugu ucaauaaagc   1200
cuguccaugc cuugauacua uaucacuucu cacucuugac aauugcauuu cugcagcugu   1260
aagcuuguug uccucaccua cgauccuuau ugaccgucca uaaccuuuga uugauagauc   1320
aauuggacca guaguaaauu cucgagaugu uugccaguua uuccauguga ucugcucuuc   1380
ugcuuuuucu gcaucaaauc ugucaacguc uauuuguugc aaaucgccca ggugauauaa   1440
uaaugguaua auuuuugaac guagucucga auuuuugauu uucuuguaga gacuggauac   1500
uugaacaucc uuguauguau auguguuaau aauugcauua auauaagcuu uuuuggaguc   1560
aucauuuagg aacauaucag caaaaugugc aauuagccug aaacauucgu aggcuauuug   1620
uauuuccaga ucuauagaug uggcuauuug ugccuucuuu gcugggacag uuauuuguuu   1680
uaaauaguga acaaccaucc auuuguuguc ugauaucaga uuaccuguua cuaaugagca   1740
gaaaucaaug ggaguguaag ccuuuuuugg aaggaugaau auuuuaauuu uguguucugu   1800
ugauuucaca uauucauaac agaucugaua gaauuuaguc aauuccugca cuucaaauuu   1860
caaaucucgc uucauuaacu uaauuucauu auuugcaauu cucccuugca uauuuguccu   1920
caauuuuguc uucucuauaa auucuucuaa augauauaua ucucuccgca uuucaucugg   1980
cuccaucccu uuuugcucau aguuaucugu uacauaagca cguaauacga gagcaggacu   2040
augauaaauu acuuuaaggc ucuuaaucuc cggcauauaa cagcauguca uacccaaucg   2100
uugcaucucc acucccugua uugaaauuaa caaguuguuu gcacaagcaa cuaauauagg   2160
gucguucauu auacagaagc uauauaucgu cuuuauaucc ucuacaucaa guguaaauuu   2220
uucuacauca auuuuuauuu gcugauaugu uucaacaaaa gucuucuugc caauaaauaca  2280
uguagcauca uuuauauuug ggucaucuug uauaccaaac aaccuaucau gaauacuugu   2340
auagucuauc auugguuuau uugcaaacaa uacuuguucu augaagagcu gagcuggguu   2400
uugaauagac aaugauucuu uaaauuuacg acuguuguau cugaacaaua cagacauaca   2460
gaacucuuca caagucucac cuuuuguaac caauaguuga ggguuggcua uaaaauauuc   2520
aaauaauucu ucaauuuucu guuggucuug uauuguuuuu ugauaaucag cauaugaaug   2580
caaucuagau aacgaacuug caguagugaa uuuucuuggu gucagaagag accuagaucu   2640
cauuucacua guuucgccca uuccaucauc agaugacaua guugagucua acgucaugua   2700
ucuuaaaagc uuaagucuga aaauaucaca uugugucagu uuacuuauau cccauguaug   2760
```

-continued uauauucuca uauugaugcu ggauugguuc acggcaaaga uguauagggg acauucuuuu 2820
ugauaaccua acuaaauaac uuagauuauc ugcuuccaaa ccugcuauag cuauaguggg 2880
uaauucugaa uuuauuaagc cacacaauuc uauaggcagc ucaaaucuau caugacuagg 2940
uaaagaugaa guaggaucau ugauuugacc uggaagcaug uuauaugugc uauguguuau 3000
ccacugaguu aaugcaauag caguccaugc aagugaugga ggugcuccau gcuuaauugc 3060
ugucugcguu gcagacaacc uacuggcaac auccucauau gguccaagaa aagcacaauc 3120
gccaacagau gucaaaauaa agcgaccaua aacagaaaau ggcucaccau aaauauuaaa 3180
aagugaaacg aacuccuuua ugaaauuugu uauauauguc uucuucauau uugcuugauu 3240
uccaaaaguu agacauauuu uuucaaauag uuuugcagaa aauucaauaa caauaucauc 3300
aucuaauuua ucuuggauca ucacuauuga agugugauug ucaucagaau gaaccauaga 3360
auugacuaaa acuuccccuu cuaguaaagu ggcugcucuc uuuagaauau ccuuauaaac 3420
auucauagaa caugaaugua gguagcuacu uguguaauug agauuccccu gcagccaguu 3480
ccguuuaaua uugacccaau uuugcgauaa gccauugguc auuucauaua uuauaucauc 3540
cucauguuug auacguuggu caaggaugcu acagagcauu ucaucaggca gaauuagcuu 3600
uuuuugcaua uaauugcaua ggaaguacaa uauccuuucu uuuucuugca gauaaagugc 3660
gggaucuaau gcaaacaacc agaaauauuu gaauaaaaca ucuugggcac uccauuuuga 3720
caugucugca uugauuucaa ucuuaacaga auggguuua uaugcgauca uauggcuugc 3780
uucucccauu ucugcuaaau agcguucuuu gaucuguuuc auaguugcug cugugaaucg 3840
uauuucagac ucugcaagcu cuucuaauuu uuucaauuua gaaucgccug guucacuaau 3900
caucucaucu ggauucaacu uacagcguuc uuuagauauc cucuccacua aauacaagca 3960
cauuuuugcc ucaaauucgc cuacgaauau uucccuaucc uuugcuguuu uuuggccuuu 4020
guuaaagaau guaaacuuaa aaucugugug auucuucaua gcagagagua uaugauacac 4080 agugggguuua ucaucuaucu ccuuccuuuu uauuuucugg uacagagaau caaauacuuu 4140
aguugacaua augucaauau aauucgggau ugcuuuuuuu aagucuucau agcgugaaug 4200
ucuuauaguu gcauuuagua acucuucauc aacaaauucu ggguuugcaa uuguauacuu 4260
cuuuaucucu uuugacaugc aaucugcagc cuuuuuuguu gcugagcuuu uuucuuucuc 4320
aaagucgccu acuuuaauac augauuuaga gcuggugaau guagaaauag ugcauaucga 4380
ucuauuuaag uuguuugugu uuucuauccg ugaucuaaua uaauuauguc uagcaguguc 4440
cauuauuaga uuuuuugcaa cugcauagau aguuauauuu aaauuugcag uuuguuuucu 4500
agguguugua gaccauauuc cugggauauu uaaucucugg ucccuuucua uaucuaagau 4560
ugucuuagcc agaucuauca uaacaugaug cuuuucaugc aaaccuuuug aauugaagua 4620
aaaugguaga uauauuuggu uaauauauuc uuuuagugau acauagccuu caaaccagau 4680
ugaugauagg ucucuguuau cucucacacc uuuuugaguu auuucauaau cuguuaggca 4740 gauauucuc augucuacuu uaucucuuug auuauaugcc auauaacauc cccuuuuaau 4800
caaguuugcc auuacuacag agaagcuggu cuuuguauaa gggccaaauu uuucugcuau 4860
auaaucucua acaugacugg auauggcuaa ugaauucauu aucauauauc uugaugguuc 4920
ugucaaugac agcauagcuu ugguuauaga cagggaagug uggaauguaa aauucaugac 4980
aucagucaaa uugagugucg gauugucucc ugcaaacauc aauguaguca acauaaaaag 5040
ucccggugaa cuaacuaugc guugacaucg uucuuuaucu aaacgcauuc cuuuagagau 5100

-continued acuaagguau uuugaaccag uuuuaaaugu cgcaugcaau gcaccguggu gcaucacauu 5160
cugaggagua gaaugcaaca cagcuaagaa guaaacaagu guggaucgcu uugcuuuaau 5220
aucagaagaa ggcauuacaa acccaaacag auuauuguuu gcacaacaca cuacacgaaa 5280
aguauugugc cuauuauauu gagaaacugc caacauauuu uucaucaaga cugaaaaauc 5340
uuuaauacaa gcccaguaau uugacuuccc uaucugguua aucugauccc auguauccuu 5400
ugaacaugau gcaauauuug caccauauuc uucuaaauaa cauccuauac gcucuagauu 5460
auuaucuccg gauaguauuu ucuuuacauu uucauacugg aauuugcaaa aaucaaugac 5520
uuccuuuuug uugaaaucua auauaguagg uuugucagua uccaaaucgu caauggucuu 5580
uuuugaaaau ugcacgugac ccccuaugcc aagaaaaucu uuuagcaaau gugauuuguc 5640
uuuuguauuc auuauuucag uauccaguuu aaacugcugu ucccaauaaa uugucgccgu 5700
gccuauuuug auugguucca guuuaguauc aauucuuuuc gaugucuguc uugccauacu 5760
uuuuaguuug cuagugugug cuucauauaa agcuguguuc ucagaaaagu ccauaagcau 5820
acccaaugcu cugaaugcgc uuauauaugu agacucgcca gaaauauuuu ggagugcuuu 5880
ugcaaucuug auuaguuuug guguugucgc auuugauguu ucgucagguu gaccccauau 5940
gaaaugaaua gaugguuuuu gcuugcugac aucuugaguc agguuucucu caguacucac 6000
ucuuugaacc auuugauucc aaccgauugu gauuucauca ugauuugguu uuggguaguu 6060
cccuucacau cuaaagauuc cugcagcggc cucuuucaca aaaauguuau aaucauugcc 6120
auaucuauuu auaaccuuuu guagauuuug auuccauuuc ucaccgcgag uugcaucaaa 6180
ugucauagac ucauggaaug ucaguuuagc caucucaucu aaagaaucau agaauuccaa 6240
aaagacaggg ugugaauaga gcuccggggu auccucauca auccagggug cagucaucgu 6300
aaauucaccu ugauucacaa uuucuaggaa ucugucguca uccuuauauu ucucauauau 6360
cagggaucgc aaauuaaaga accaaguaaa aucaagguuu auguugagcg gcccaaauau 6420
uuccaagaau ugauuugaau uaacauggau aguaucucgc agagggucag cacggaugau 6480
cacaacuuca aaaucaaacg gcaauucuga caaugcgucu ccaaagaucu ggguguacuu 6540
uucauaaguu uuuugaccau augcaugauc aguugauacu uuauagucaa ugauauaaag 6600
cuugccauug ugaaugauaa aauugucugg uguacaauug cgaauguuga aagcagugcc 6660
agcuggcaga aauucaagaa guaugucgua agcuggaaca uccugccgga auucgauauc 6720
cagguaauaa cauaccucuc uaccaaagua gucaugucua gccaugagaa gaucagcaac 6780
aaugucuuug gcuucuucag cacuucgaca cugguugauc cuaucucuaa aaauguuaau 6840
cuuguauguc uccauaguga uuguaauuag ggguacacua cu 6882

<210> SEQ ID NO 7
<211> LENGTH: 839
<212> TYPE: DNA
<213> ORGANISM: Schmallenberg virus

<400> SEQUENCE: 7
agtagtgaac tccactatta actacagaaa tatgtcaagc caattcattt ttgaagatgt 60
accacaacgg aatgcagcta catttaaccc ggaggtcggg tatgtggcat ttattggtaa 120
gtatgggcaa caactcaact tcggtgttgc tagagtcttc ttcctcaacc agaagaaggc 180
caagatggtc ctacataaga cggcacaacc aagtgtcgat cttacttttg gtggggtcaa 240
atttacagtg gttaataacc attttcccca atatgtctca aatcctgtgc cagacaatgc 300
cattacactt cacaggatgt caggatatct agcacgttgg attgctgata catgcaaggc 360

-continued

```
tagtgtcctc aaactagctg aagctagtgc tcagattgtc atgccccttg ctgaggttaa    420

gggatgcacc tgggccgatg gttatacaat gtatcttgga tttgcacctg gggccgaaat    480

gttccttgat gcttttgact tctatccact agttattgaa atgcataggg tcctcaagga    540

caatatggat gtaaatttta tgaaaaaagt cctccgccaa cgctatggaa caatgactgc    600

tgaagaatgg atgactcaga aaataacaga aataaaagct gcttttaatt ctgttggaca    660

gcttgcctgg gccaaatctg gattctctcc tgctgctaga accttcttgc agcaattcgg    720

tatcaacatc taaacctctt catcacagat cttcaatttc cgtgcaatat gtctatgtat    780

tgcacaccat tatactgcaa ggcttctgtt aagatagtta ataagtggag aacactact     839


<210> SEQ ID NO 8
<211> LENGTH: 839
<212> TYPE: RNA
<213> ORGANISM: Schmallenberg virus

<400> SEQUENCE: 8

aguaguguuc uccacuuauu aacuaucuua acagaagccu ugcaguauaa uggugugcaa     60

uacauagaca uauugcacgg aaauugaaga ucugugauga agagguuuag auguugauac    120

cgaauugcug caagaagguu cuagcagcag gagagaaucc agauuuggcc caggcaagcu    180

guccaacaga auuaaaagca gcuuuuauuu cuguuauuuu cugagucauc cauucuucag    240

cagucauugu uccauagcgu uggcggagga cuuuuuucau aaaauuuaca uccauauugu    300

ccuugaggac ccuaugcauu ucaauaacua guggauagaa gucaaaagca ucaaggaaca    360

uuucggcccc aggugcaaau ccaagauaca uuguauaacc aucggcccag gugcaucccu    420

uaaccucagc aaggggcaug acaaucugag cacuagcuuc agcuaguuug aggacacuag    480

ccuugcaugu aucagcaauc caacgugcua gauauccuga cauccuguga aguguaaugg    540

cauugucugg cacaggauuu gagacauauu ggggaaaaug guuauuaacc acuguaaauu    600

ugaccccacc aaaaguaaga ucgacacuug guugugccgu cuuauguagg accaucuugg    660

ccuucuucug guugaggaag aagacucuag caacaccgaa guugaguugu ugcccauacu    720

uaccaauaaa ugccacauac ccgaccuccg gguuaaaugu agcugcauuc cguugguggua    780

caucuucaaa aaugaauugg cuugacauau uucuguaguu aauaguggag uucacuacu     839
```